United States Patent
Tajima et al.

(10) Patent No.: US 9,579,076 B2
(45) Date of Patent: Feb. 28, 2017

(54) RADIATION IMAGE DETECTING DEVICE AND RADIATION IMAGING SYSTEM

(71) Applicant: FUJIFILM Corporation, Tokyo (JP)

(72) Inventors: Takashi Tajima, Ashigarakami-gun (JP); Takeshi Kuwabara, Ashigarakami-gun (JP); Yusuke Kitagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 260 days.

(21) Appl. No.: 14/511,440

(22) Filed: Oct. 10, 2014

(65) Prior Publication Data
US 2015/0030129 A1 Jan. 29, 2015

Related U.S. Application Data

(63) Continuation of application No. PCT/JP2013/060921, filed on Apr. 11, 2013.

(30) Foreign Application Priority Data

Apr. 20, 2012 (JP) ................................ 2012-096277

(51) Int. Cl.
*H05G 1/42* (2006.01)
*A61B 6/00* (2006.01)
(Continued)

(52) U.S. Cl.
CPC ........... *A61B 6/4291* (2013.01); *A61B 6/4208* (2013.01); *A61B 6/4283* (2013.01); *A61B 6/542* (2013.01); *H05G 1/44* (2013.01); *G21K 1/02* (2013.01)

(58) Field of Classification Search
CPC ..... A61B 6/4291; A61B 6/4209; A61B 6/542; A61B 6/4208; A61B 6/4283; H05G 1/44; G21K 1/02
(Continued)

(56) References Cited

U.S. PATENT DOCUMENTS

| 6,944,266 B2 | 9/2005 | Yamazaki et al. |
| 6,952,465 B2 | 10/2005 | Hirai et al. |
| 2004/0096035 A1* | 5/2004 | Yamazaki .............. A61B 6/107 378/97 |

FOREIGN PATENT DOCUMENTS

| JP | 2004/166724 A | 6/2004 |
| JP | 2004-166724 A | 6/2004 |
| JP | 2004-167075 A | 6/2004 |

OTHER PUBLICATIONS

Japanese Office Action and English translation thereof, dated Dec. 9, 2015, for corresponding Japanese Application No. 2013-081647.
(Continued)

*Primary Examiner* — Courtney Thomas
(74) *Attorney, Agent, or Firm* — Birch, Stewart, Kolasch & Birch, LLP

(57) ABSTRACT

A detection panel has a plurality of pixels for accumulating electric charge by receiving X-rays, and a plurality of detection pixels for detecting an X-ray dose in an imaging surface. The detection pixels are disposed periodically with leaving space. A grid, which has X-ray absorbing portions and X-ray transmitting portions alternately and periodically arranged in a first direction, is disposed in a position opposed to the imaging surface. Since an arrangement period of the detection pixels in the first direction is different from an arrangement period of the X-ray absorbing portions, an output value of each detection pixel is distributed and hence the average of the output values has a reduced variation range.

13 Claims, 22 Drawing Sheets

(51) Int. Cl.
*H05G 1/44* (2006.01)
*G21K 1/02* (2006.01)

(58) Field of Classification Search
USPC .......................................................... 378/62
See application file for complete search history.

(56) References Cited

OTHER PUBLICATIONS

Chinese Office Action and Search Report, issued in Chinese Application No. 201380020938.3, dated Feb. 16, 2016, including English Translation.
International Search Report, issued in PCT/JP2013/060921, dated May 14, 2013.
Written Opinion of the International Searching Authority, issued in PCT/JP2013/060921, dated May 14, 2013.
Chinese Office Action for Chinese Application No. 201380020938.3, dated Jun. 17, 2016, with an English translation.

\* cited by examiner

FIG. 10 <COMPARATIVE EXAMPLE>
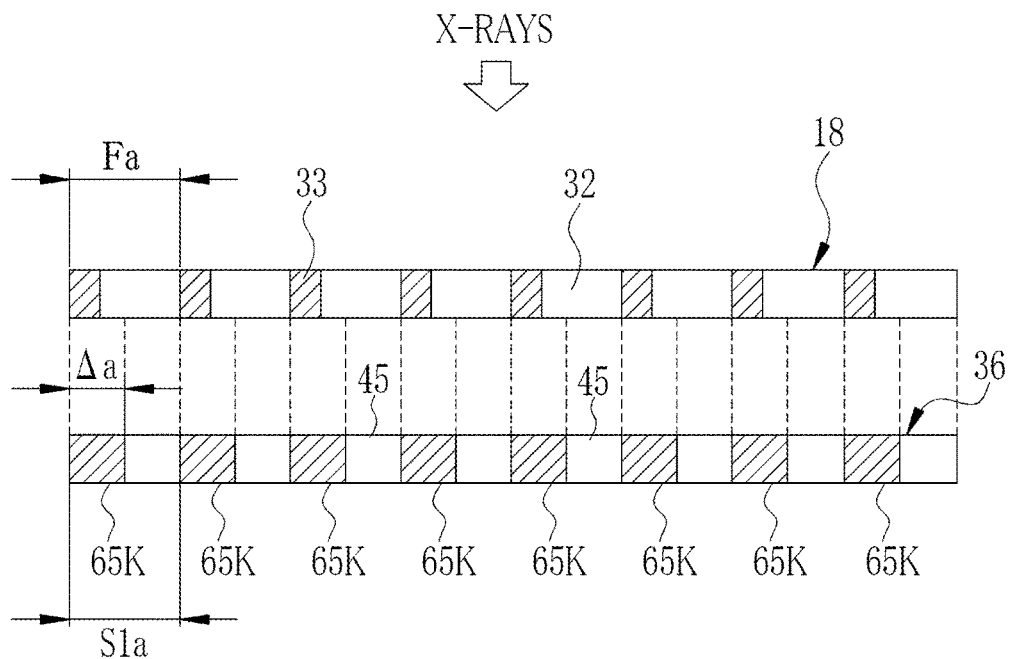
FIG. 11 <COMPARATIVE EXAMPLE>
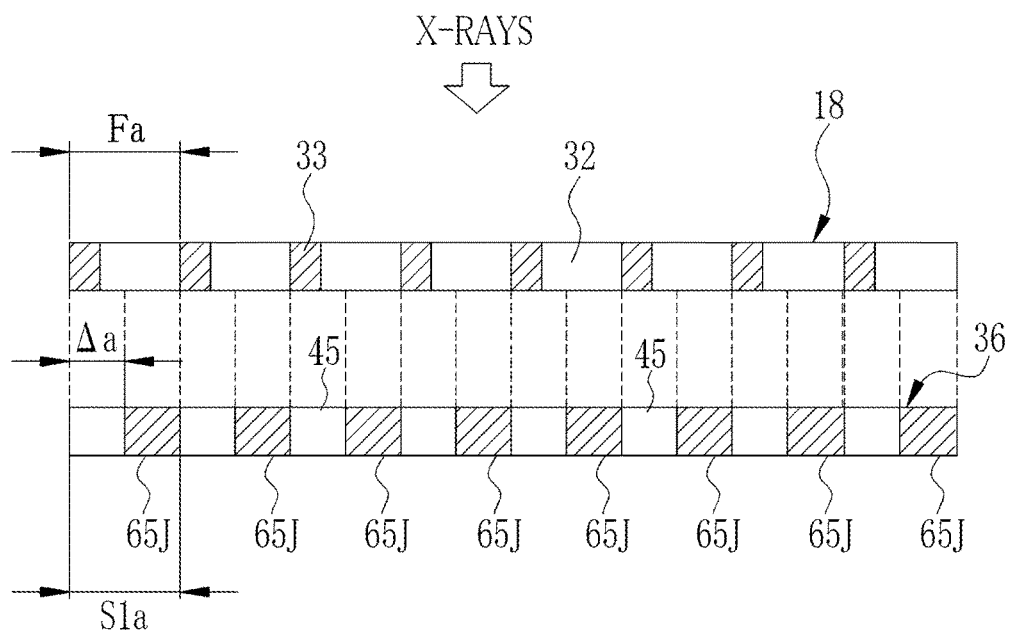

FIG. 12 <COMPARATIVE EXAMPLE>
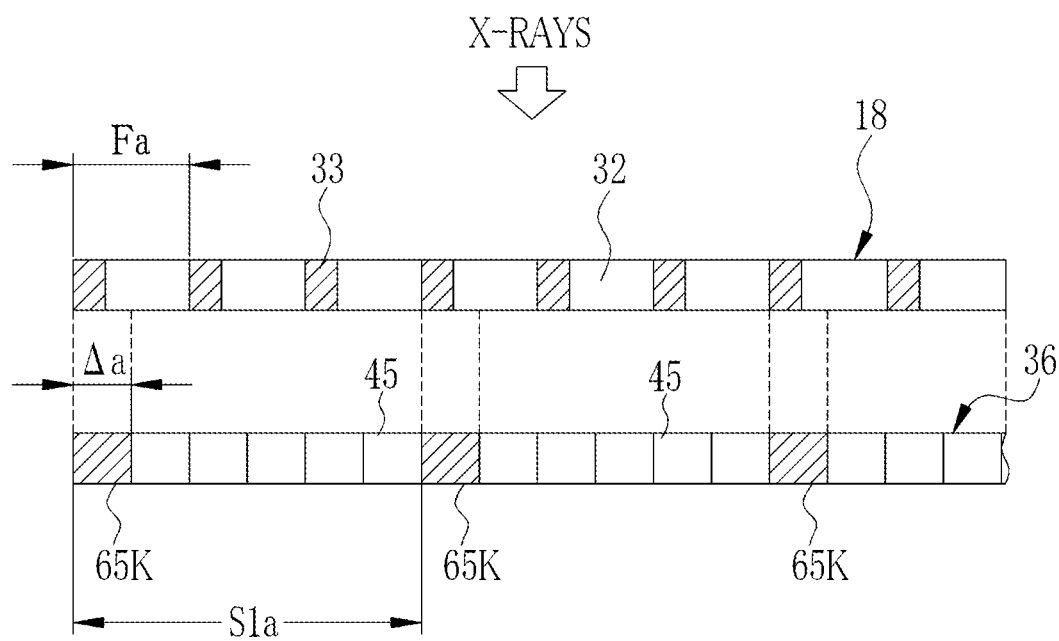

FIG. 15
| BODY PART | TUBE VOLTAGE (kV) | TUBE CURRENT (mA) | MEASUREMENT AREA | EMISSION STOP THRESHOLD VALUE |
|---|---|---|---|---|
| ... | ... | ... | ... | ... |
| CHEST | V1 | I1 |  | TH1 |
| ABDOMEN | V2 | I2 |  | TH2 |
| ... | ... | ... | ... | ... |

RADIATION IMAGE DETECTING DEVICE AND RADIATION IMAGING SYSTEM

CROSS-REFERENCE TO RELATED APPLICATIONS

This application is a continuation of PCT International Application No. PCT/JP2013/060921 filed on Apr. 11, 2013, which claims priority under 35 U.S.C. 35 §119(a) to Japanese Patent Application No. 2012-096277 filed on Apr. 20, 2012. Each of the above applications is hereby expressly incorporated by reference, in its entirety, into the present application.

BACKGROUND OF THE INVENTION

1. Field of the Invention

The present invention relates to a radiation image detecting device having a dose detection sensor for performing exposure control of a radiographic image, and a radiation imaging system using the radiation image detecting device.

2. Description Related to the Prior Art

In a medical field, a radiation imaging system, for example, an X-ray imaging system using X-rays as a kind of radiation is known. The X-ray imaging system is constituted of an X-ray generating device for producing the X-rays, and an X-ray imaging device for taking an X-ray image of an object by receiving the X-rays passed through the object (patient). The X-ray generating device has an X-ray source for emitting the X-rays to the object, a source control device for controlling the operation of the X-ray source, and an emission switch for inputting to the source control device a command to operate the X-ray source. The X-ray imaging device has an X-ray image detecting device for detecting the X-ray image based on the X-rays passed through the object, and a console, for controlling the operation of the X-ray image detecting device and saving and displaying the X-ray image.

As the X-ray image detecting device, a flat panel detector (FPD) for detecting the X-ray image as an electric signal has come into widespread use. The FPD includes a detection panel having an imaging surface having a matrix of pixels for accumulating electric charge in accordance with an X-ray dose incident thereon and circuitry for operating the detection panel. The detection panel accumulates the signal charge on a pixel-by-pixel basis and converts the accumulated electric charge into a voltage signal by a signal processing circuit, to detect the X-ray image of the object and output the X-ray image as digital image data. Also there is a portable type X-ray image detecting device called electronic cassette, which contains the FPD in a cassette housing.

In the X-ray imaging, there are cases where a scattered radiation removing member called grid is used for the purpose of reducing the influence of scattered radiation that is produced by the X-rays in passing through the object. The grid is disposed between the object and the X-ray image detecting device. The grid is composed of X-ray absorbing portions and X-ray transmitting portions arranged alternately. Each X-ray absorbing portion is made of an X-ray absorbing and opaque material such as lead into the shape of a slender strip. Each X-ray transmitting portion is made of an X-ray transparent material such as aluminum into the shape of a slender strip. Since the X-ray absorbing portions and the X-ray transmitting portions are arranged alternately in one direction, the X-ray absorbing portions and the X-ray transmitting portions form a stripe pattern. Such a grid is disposed between the imaging surface of the detection panel and the object. The use of the grid facilitates obtaining a high-contrast image with reduced influence of the scattered radiation, because most of the scattered radiation is absorbed by the X-ray absorbing portions in the grid before reaching the imaging surface. The grid is attached to an imaging stand or a housing of the X-ray image detecting device in use.

One of items representing the type of the grid is a grid density that represents the number of the X-ray absorbing portions per unit width. There are various grid densities within the confines of 26/cm 100/cm, for example. Taking the case of a grid density of 40/cm (4/mm) as an example, a grid pitch, being the sum of the width of a pair of X-ray absorbing portion and X-ray transmitting portion is 250 μm.

Some X-ray image detecting devices have an automatic exposure control (AEC) function, which stops an X-ray emission from the X-ray source at the instant when an X-ray dose emitted from the X-ray source has reached a predetermined emission stop threshold value, in order to perform exposure control of the X-ray image (refer to U.S. Pat. No. 6,952,465 corresponding to Japanese Patent Laid-Open Publication No. 2004-167075 and U.S. Pat. No. 6,944,266 corresponding to Japanese Patent Laid-Open Publication No. 2004-166724, for example). Such X-ray image detecting devices have dose detection sensors, which detect an X-ray dose passed through the object and output a signal corresponding to the detected dose.

The U.S. Pat. No. 6,952,465 describes an X-ray image detecting device that is provided with stripe-shaped dose detection sensors having a length of 500 pixels in an imaging surface of a detection panel, besides pixels. According to the U.S. Pat. No. 6,952,465, the dose detection sensors are disposed such that a longitudinal direction (stripe direction) of the striped dose detection sensors is not in parallel with (for example, orthogonal to) a stripe direction of a grid. Accordingly, even if misalignment occurs in geometrical disposition being the positional relation between the grid and the dose detection sensors, stable AEC is performed by reducing variation in an output value of a signal outputted from the dose detection sensor.

In other words, since the dose detection sensors are disposed in the imaging surface, the misalignment occurs in the geometrical disposition between the grid and the dose detection sensors owing to an attachment backlash of the grid, a manufacturing error of the grid, and the like. Each of X-ray absorbing portions and X-ray transmitting portions of the grid has a width of the order of micrometers. Thus, the attachment backlash or the manufacturing error of the grid easily causes the misalignment of the order of one X-ray absorbing portion or one X-ray transmitting portion between the grid and the dose detection sensors. The misalignment in the geometrical disposition between the grid and the dose detection sensors causes variation in the amount of X-rays incident upon the dose detection sensors, even if an X-ray emission amount is the same, and hence results in variation in the output value of the dose detection sensor. A variation range of the output value of the dose detection sensor is maximized in a case where the stripe direction of the dose detection sensors is in parallel with the stripe direction of the grid.

For example, in a case where the stripe direction of the dose detection sensors is in parallel with the stripe direction of the grid, the striped dose detection sensors may be hidden behind the X-ray absorbing portions throughout its longitudinal direction, or contrarily situated behind the X-ray transmitting portions. In a case where the entirety of the dose detection sensor is hidden behind the X-ray absorbing portion, the X-ray incident amount is reduced throughout the dose detection sensor, and hence the output value of the dose detection sensor is minimized. On the contrary, even if the X-ray emission amount is the same, in a case where the entirety of the dose detection sensor is situated behind the X-ray transmitting portion, the X-ray incident amount is increased throughout the dose detection sensor, and hence the output value of the dose detection sensor is maximized. As described above, paralleling the stripe direction of the dose detection sensors to the stripe direction of the grid increases the variation range of the output value of the dose detection sensor caused by the misalignment in the geometrical disposition between the grid and the dose detection sensors.

Thus, according to the U.S. Pat. No. 6,952,465, the striped dose detection sensors are disposed not in parallel with the stripe direction of the grid, so that a part of the dose detection sensor is always disposed behind the X-ray absorbing portion and another part of the dose detection sensor is always disposed behind the X-ray transmitting portion, even if the geometrical disposition between the grid and the dose detection sensors is misaligned. Thereby, the X-ray incident amount is relatively low at a part of the dose detection sensor, while relatively high at another part of the detection sensor, so the output value of the dose detection sensor is leveled. Therefore, as compared with the case of paralleling the stripe direction of the dose detection sensors to the stripe direction of the grid, it is possible to prevent the variation in the output value of the dose detection sensor caused by the misalignment in the geometrical disposition between the grid and the dose detection sensors, and carry out the stable AEC.

In an embodiment of the U.S. Pat. No. 6,952,465, a pixel is of a size of 105 μm×105 μm. The dose detection sensor has a size of 500 pixels, and hence a length of the order of 105 μm×500=52500 μm (approximately 50 mm). The dose detection sensor is substituted for the pixels, or disposed in space between the adjoining pixels. In the case of disposing the dose detection sensor in the space between the pixels, the pixels adjoining to the dose detection sensor are downsized, to secure space for the dose detection sensor. A plurality of the dose detection sensors is disposed in a predetermined area.

Also, the U.S. Pat. No. 6,944,266 describes an X-ray image detecting device in which detection pixels (referred to as AEC pixels in the U.S. Pat. No. 6,944,266) functioning as dose detection sensors are substituted as some of pixels, instead of providing the striped dose detection sensors. The U.S. Pat. No. 6,944,266 uses so-called non-destructive readout pixels from which an output value is read out while the pixels keep holding accumulated electric charge, and the detection pixels are also read out in a non-destructive manner.

In the U.S. Pat. No. 6,944,266, since the detection pixels are disposed in an imaging surface, misalignment in the geometrical disposition between a grid and the detection pixels causes variation in an output value of the detection pixel, just as with the U.S. Pat. No. 6,952,465. The U.S. Pat. No. 6,944,266 deals with the problem of variation in the output value of each detection pixel by calibration, which calibrates the output value of each detection pixel.

To be more specific, according to the U.S. Pat. No. 6,944,266, the X-rays are evenly applied to the imaging surface having the grid attached, to obtain a gain image representing the output value of each detection pixel in the imaging surface. In the gain image, variation in the output values of the detection pixels in a state of attaching the grid is reflected. In AEC of actual imaging, the output value of each detection pixel is calibrated with the gain image to correct the output value of each detection pixel. The output value of each detection pixel varies with not only the type of the grid specifying the grid density, but also an imaging condition including an X-ray dose and X-ray quality depending on a tube voltage. Even if the type of the grid and the imaging condition are the same, an attachment backlash of the grid or a manufacturing error causes misalignment in the geometrical disposition between the grid and the detection pixels, so that the gain image is obtained whenever imaging is carried out.

In the U.S. Pat. No. 6,952,465, the space for the striped dose detection sensors is secured by substituting or downsizing the pixels, so the obtained X-ray image has low density at portions corresponding to the dose detection sensors. The difference in density is large between the portion corresponding to the dose detection sensor and other portions adjoining thereto, and hence manifests itself as a strip of density step. Since the striped dose detection sensors have a length of approximately 50 mm, being a size visible to a human eye, the density step of the X-ray image is also of a size visible to the human eye and very conspicuous. To eliminate such a density step, the U.S. Pat. No. 6,952,465 discloses performing a defect correction with regarding the dose detection sensors as defect pixels, but a defect correction requires an effort at preparing correction data. Furthermore, the dose detection sensors are large, being approximately 50 mm. Thus, it is difficult to completely eliminate the defect by the defect correction to the extent of being invisible, and it is feared that the image quality of the X-ray image may be degraded.

In the case of the U.S. Pat. No. 6,944,266, some of the pixels are used as the detection pixels and the output values of the detection pixels are read out in a non-destructive manner, so no density step occurs in the X-ray image, in contrast to the U.S. Pat. No. 6,952,465. Therefore, there is no problem of efforts at the defect correction and no problem of degradation in the image quality of the X-ray image. However, in the case of the X-ray image detecting device described in the U.S. Pat. No. 6,944,266, the gain image has to be obtained whenever imaging is carried out, and hence there is another problem that obtaining the gain image requires time and effort. Furthermore, if the geometrical disposition between the grid and the detection pixels is misaligned after obtainment of the gain image and before carrying out actual imaging, the correction cannot be performed appropriately with the obtained gain image.

SUMMARY OF THE INVENTION

An object of the present invention is to provide a radiation image detecting device and a radiation imaging system that can perform stable AEC that is insusceptible to misalignment in geometrical disposition between a grid and dose detection sensors with having little fear of degradation in image quality and requiring no time and effort.

A radiation image detecting device according to the present invention includes a detection panel and a plurality of dose detection sensors, and carries out imaging by using a scattered radiation removing grid having radiation absorbing portions for absorbing radiation and radiation transmitting portions for transmitting the radiation alternately and periodically arranged in a first direction. The detection panel has an imaging surface provided with a plurality of pixels for converting the radiation into an electric signal, and detects a radiographic image of an object. The plurality of dose detection sensors are provided for performing exposure control of the radiographic image. The plurality of dose detection sensors is disposed in the imaging surface periodically with leaving space in the first direction, for detecting a dose of the radiation passed through the object and outputting a signal in accordance with the dose. An arrangement period of the radiation absorbing portions is different from an arrangement period of the plurality of dose detection sensors in the first direction in the imaging surface.

It is preferable that the arrangement period of the dose detection sensors be not an integral multiple of the arrangement period of the radiation absorbing portions.

It is preferable that each of the arrangement period of the dose detection sensors and the arrangement period of the radiation absorbing portions have a length in unit of the number of the pixels, and the arrangement periods be co-prime numbers.

It is preferable that an arrangement period of the dose detection sensors in a second direction orthogonal to the first direction be also different from the arrangement period of the radiation absorbing portions. The arrangement period of the dose detection sensors in the second direction is preferably the same as the arrangement period of the dose detection sensors in the first direction.

A minimum size of the dose detection sensor is preferably the same as the size of the pixel in the imaging surface.

It is preferable that the dose detection sensors be detection pixels as which some of the pixels are utilized. In a case where a plurality of the detection pixels are disposed with being shifted by one or more rows and one or more columns in each of a row direction corresponding to the first direction and a column direction corresponding to the second direction, the arrangement period in the first direction is preferably a length in the row direction, and the arrangement period in the second direction is preferably a length in the column direction. The dose detection sensor is preferably a detection pixel group composed of a plurality of the detection pixels adjoining each other.

It is preferable that the dose detection sensor output the signal in accordance with the dose per unit of time, and the radiation image detecting device further include an automatic exposure control section for integrating an output value of the dose detection sensor, and comparing an integral value with an emission stop threshold value set in advance, and stopping emission of the radiation from a radiation source upon the integral value reaching the emission stop threshold value. The automatic exposure control section preferably calculates an average of the output values of a plurality of the dose detection sensors, and obtains the integral value by integrating the calculated average.

It is preferable that the scatter radiation removing grid be detachably attached.

A radiation imaging system according to the present invention includes a radiation generating device having a radiation source for emitting radiation and a radiation image detecting device for detecting a radiographic image, and carries out imaging by using a scattered radiation removing grid having radiation absorbing portions for absorbing radiation and radiation transmitting portions for transmitting the radiation alternately and periodically arranged in a first direction. The radiation image detecting device includes a detection panel and a plurality of dose detection sensors.

According to the present invention, the arrangement period of the plurality of dose detection sensors disposed in the imaging surface with leaving space is different from the arrangement period of the radiation absorbing portions in the grid. Accordingly, not all of the plurality of dose detection sensors is situated behind the radiation transmitting portions or the radiation absorbing portions. Therefore, it is possible to perform the stable AEC that is insusceptible to misalignment in the geometrical disposition between the grid and the dose detection sensors with having little fear of degradation in the image quality and requiring no time and effort.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 10 is an explanatory view of a first comparative example;

FIG. 11 is an explanatory view of the comparative example after a shift of one pixel from the state of FIG. 10;

FIG. 12 is an explanatory view of a second comparative example;

FIG. 15 is a diagram showing imaging conditions set in the console;

DESCRIPTION OF THE PREFERRED EMBODIMENTS

First Embodiment

Figure 1:
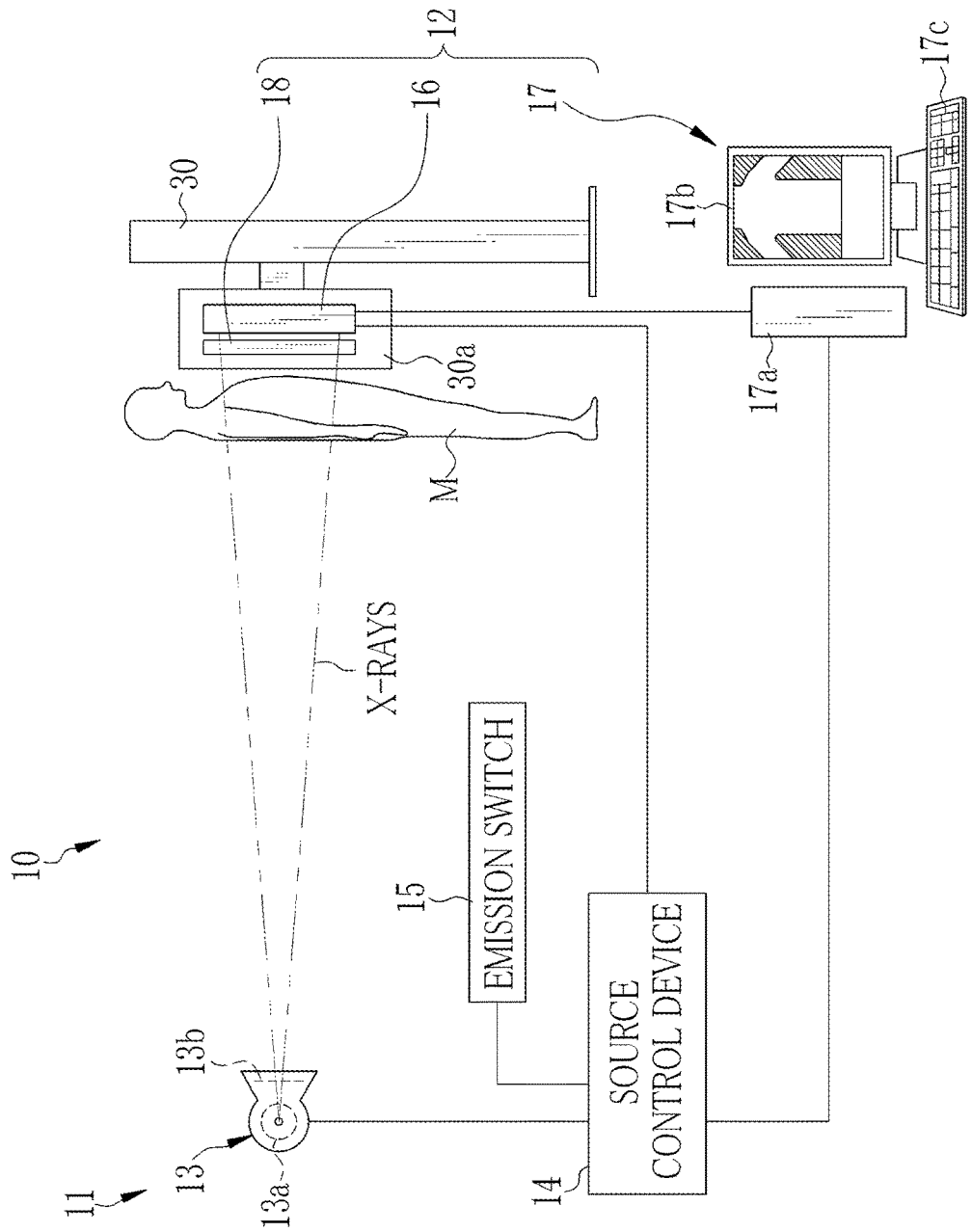
FIG. 1 is a schematic view showing the structure of an X-ray imaging system.

As shown in FIG. 1, an X-ray imaging system 10 according to the present invention is constituted of an X-ray generating device 11 for generating X-rays and an X-ray imaging device 12 for taking an X-ray image from the X-rays passed through a patient M, being an object. The X-ray generating device 11 includes an X-ray source 13 for emitting the X-rays, a source control device 14 for controlling the X-ray source 13, and an emission switch 15 for commanding the start of X-ray emission. The X-ray imaging device 12 includes an electronic cassette 16 being a portable X-ray image detecting device, a console 17 for controlling the electronic cassette 16, and an imaging stand 30. The source control device 14, the electronic cassette 16, and the console 17 are connected wiredly or wirelessly so as to be communicated with each other. An upright type imaging stand is used as the imaging stand 30 in this embodiment, but a bed type imaging stand may be used instead.

The electronic cassette 16 is detachably loadable in the imaging stand 30. The electronic cassette 16 is composed of an image detector 35 (see FIG. 4) having a detection panel 35a formed with an imaging surface 36, and a portable flat housing (not shown) containing the image detector 35. The shape of the electronic cassette 16 in plane is, for example, a square having vertical and horizontal sides of equal length.

The electronic cassette 16 is detachably set in a holder 30a of the imaging stand 30 and held in such a position that the imaging surface 36 (see FIG. 4) of the detection panel 35a is opposed to the X-ray source 13. Note that, the electronic cassette 16 is sometimes used by itself in a state of being put on a bed under the patient M lying or held by the patient M himself/herself, instead of being set in the imaging stand 30.

The X-ray imaging device 12 can perform imaging with the use of a scattered radiation removing grid (hereinafter called grid) 18 for removing scattered radiation produced at the time when the X-rays pass through the patient M. The grid 18 is a thin plate of approximately the same size as the electronic cassette 16. The grid 18 is detachably attached to the holder 30a of the imaging stand 30 together with the electronic cassette 16. The grid 18 is disposed in the holder 30a in such a position as to be opposed to the imaging surface 36 of the electronic cassette 16. Thus, the grid 18 is disposed between the patient M and the electronic cassette 16 during the imaging.

Since the grid 18 is detachable from the holder 30a, the grid 18 may be exchanged or detached from the holder 30a in X-ray imaging according to an imaging purpose. There is no mechanism for swinging the grid 18, and hence the grid 18 is a so-called static grid fixed in a set position. Note that, the grid 18 may be detachably attached to the electronic cassette 16. Also in this case, the grid 18 may be exchanged or detached in the X-ray imaging according to the imaging purpose.

The X-ray source 13 has an X-ray tube 13a for radiating the X-rays and a radiation filed limiter (collimator) 13b for limiting an irradiation field of the X-rays that the X-ray tube 13a radiate. The X-ray tube 13a has a cathode made of a filament for emitting thermoelectrons, and an anode (target) that radiates the X-rays by collision of the thermoelectrons emitted from the cathode. The radiation field limiter 13b is composed of, for example, four X-ray shielding lead plates disposed on each side of a rectangle so as to form an irradiation opening in its middle through which the X-rays propagate. A shift of the lead plates varies the size of the irradiation opening to limit the irradiation field.

Figure 2:
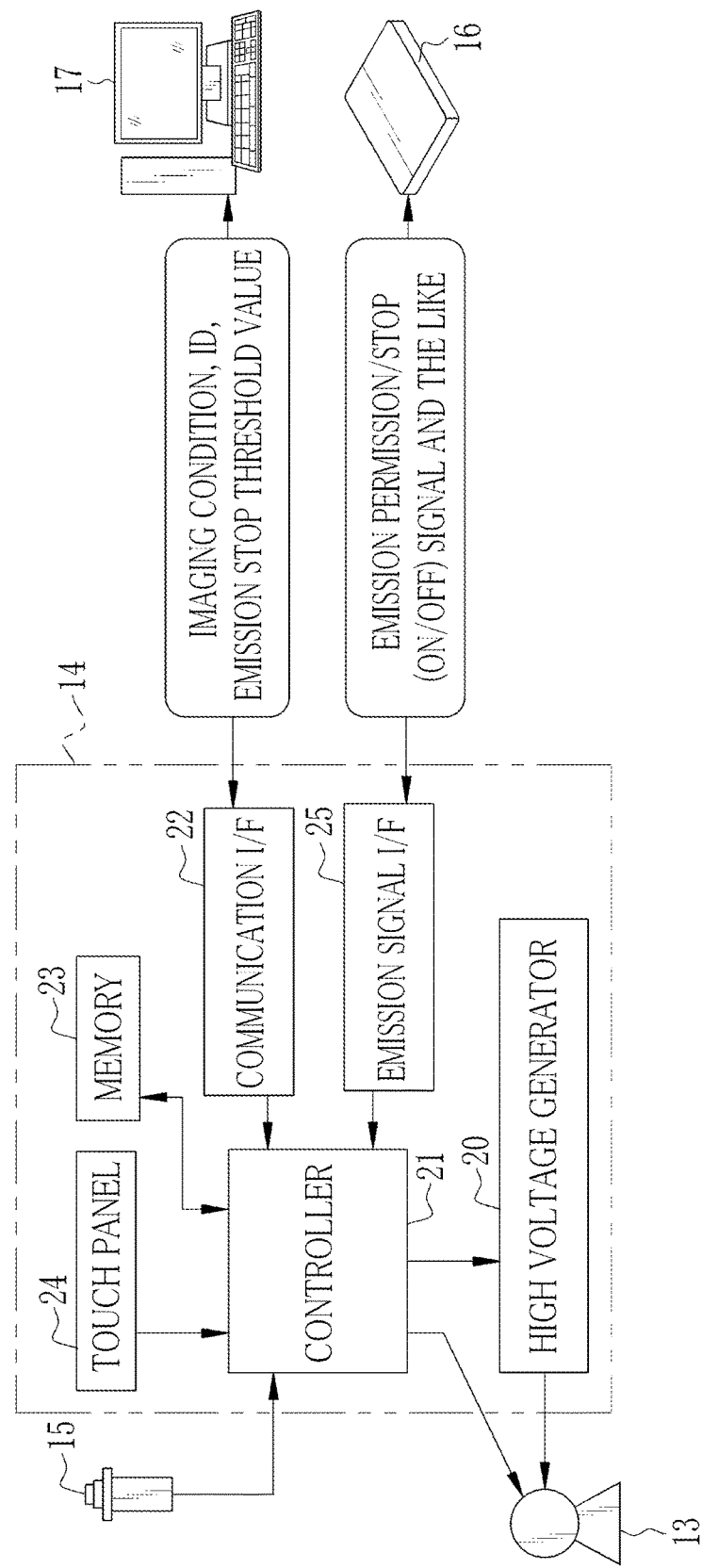
FIG. 2 is a diagram showing the structure of a source control device.

As shown in FIG. 2, the source control device 14 includes a high voltage generator 20, a controller 21, and a communication I/F 22. The high voltage generator 20 generates a high tube voltage by multiplying an input voltage by a transformer, and supplies the tube voltage to the X-ray source 13 through a high voltage cable. The controller 21 controls the tube voltage for determining an energy spectrum of the X-rays emitted from the X-ray source 13, a tube current for determining an emission amount per unit of time, and an emission time of the X-rays. The communication I/F 22 mediates transmission of primary information and signals from and to the console 17.

To the controller 21, the emission switch 15, a memory 23, and a touch panel 24 are connected. The emission switch 15 is a switch operated by an operator e.g. a radiological technician at the start of imaging, and is a two-step push switch, for example. Upon a first step push of the emission switch 15, a warm-up start signal is issued to start warming up the X-ray source 13. Upon a second step push, an emission start signal is issued to make the X-ray source 13 start the X-ray emission. These signals are inputted to the source control device 14 through a signal cable. Upon receiving the emission start signal from the emission switch 15, the controller 21 starts electric power supply from the high voltage generator 20 to the X-ray source 13.

The memory 23 stores in advance several types of imaging conditions each including the tube voltage, the tube current, and the emission time or a tube current-time product (mAs). The imaging condition is set manually by the operator through the touch panel 24. The source control device 14 starts controlling the X-ray emission based on the set imaging condition, including the tube voltage, the tube current, and the emission time or the tube current-time product. The electronic cassette 16, having an AEC function, detects a dose of the X-rays applied from the X-ray source 13 per unit of time. At the instant when it is detected that an integral dose of the X-rays has reached an adequate target value, the AEC function stops the X-ray emission even if actual emission time or actual tube current-time product is equal to or less than the value set in the source control device 14.

Note that, a value having an adequate margin is set as the emission time or the tube current-time product in the source control device 14, for the purpose of preventing a dose shortage, more specifically preventing a situation that the X-ray emission is completed, before the integral dose reaches the target value and AEC function judges the stop of the X-ray emission. A maximum value of the emission time, which is determined in accordance with a body part to be imaged under safety regulations, may be set in the source control device 14. Note that, another imaging condition that is transmitted from the console 17 through the communication I/F 22 may be set.

An emission signal I/F 25 is connected to the electronic cassette 16 in the case of using the AEC function of the electronic cassette 16. In this case, upon receiving the warm-up start signal from the emission switch 15, the controller 21 transmits an emission start request signal, which queries whether or not the X-ray emission can be started, to the electronic cassette 16 thorough the emission signal I/F 25. In response to the emission start request signal, the electronic cassette 16 performs preparation processing. After the completion of the preparation processing and standing ready to perform imaging, the electronic cassette 16 transmits an emission permission signal to the source control device 14. Upon receiving the emission permission signal from the electronic cassette 16 at the emission signal I/F 25 and further receiving the emission start signal from the emission switch 15, the controller 21 starts electric power supply from the high voltage generator 20 to the X-ray source 13 to emit the X-rays. Moreover, the controller 21 stops the electric power supply from the high voltage generator 20 to the X-ray source 13 to stop the X-ray emission, upon receiving an emission stop signal from the electronic cassette 16 at the emission signal I/F 25. Furthermore, a timer is embedded in the controller 21 to stop the X-ray emission when the set emission time has elapsed, in addition to the function of stopping the X-ray emission upon receiving the emission stop signal.

Figure 3:
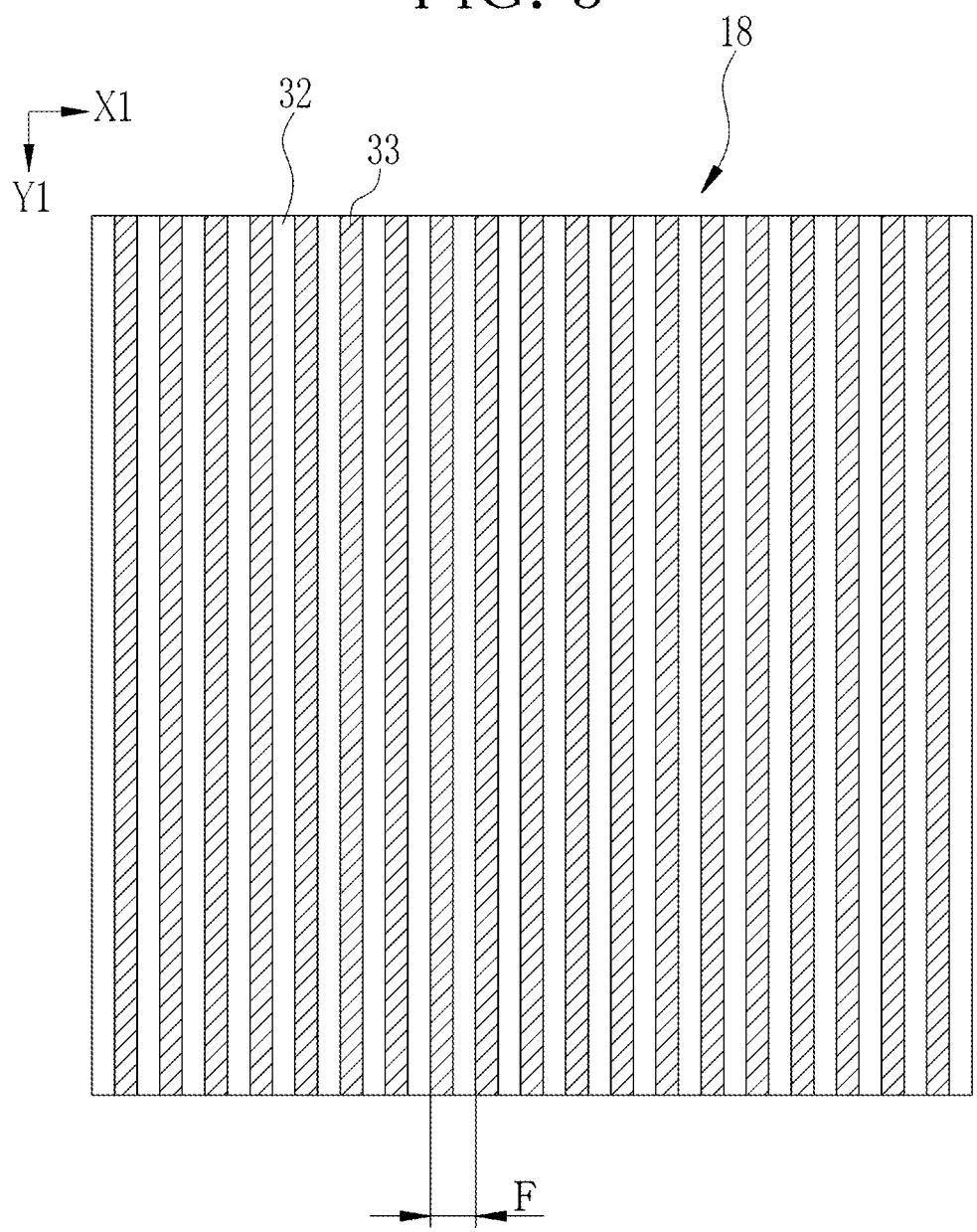
FIG. 3 is an explanatory view showing the structure of a grid.

As shown in FIG. 3, the grid 18 has approximately the same size and shape as the electronic cassette 16. The grid 18 has strip-shaped X-ray transmitting portions 32 and X-ray absorbing portions 33 shown with hatching, which extend in a Y1 direction corresponding to a second direction of the present invention. The X-ray transmitting portions 32 and the X-ray absorbing portions 33 are arranged alternately and periodically in an X1 direction, which corresponds to a first direction of the present invention, orthogonal to the Y1 direction. The X-ray transmitting portion 32 is made of an X-ray transparent material, e.g. aluminum or the like. The X-ray absorbing portion 33 is made of an X-ray absorbing material with high X-ray shieldability, e.g. lead, a molybdenum alloy, a tantalum alloy, or the like. The grid 18 absorbs at the X-ray absorbing portions 33 the scattered radiation that the X-rays produce in passing through the patient M, and thereby prevents reduction in contrast of the X-ray image caused by the scattered radiation.

The grid 18 is attached to the holder 30*a* such that the X1 direction, being an arrangement direction of the X-ray transmitting portions 32 and the X-ray absorbing portions 33, coincides with a row direction X2 (see FIG. 4) of pixels 45.

There are various types of grids 18 within the confines of a grid density, which represents the number of the X-ray absorbing portions 33 per unit width in the arrangement direction (X1 direction) of the X-ray transmitting portions 32 and the X-ray absorbing portions 33, of 26/cm to 100/cm, for example. This embodiment uses a grid having a grid density of 40/cm (4/mm), which is generally used in the X-ray imaging. A grid pitch refers to the sum of the widths (lengths in the X1 direction) of the X-ray transmitting portion 32 and the X-ray absorbing portion 33, and corresponds to an arrangement period F of the X-ray absorbing portions 33. In the case of the grid density of 4/mm, the arrangement period F of the X-ray absorbing portions 33 is 250 µm.

Figure 4:
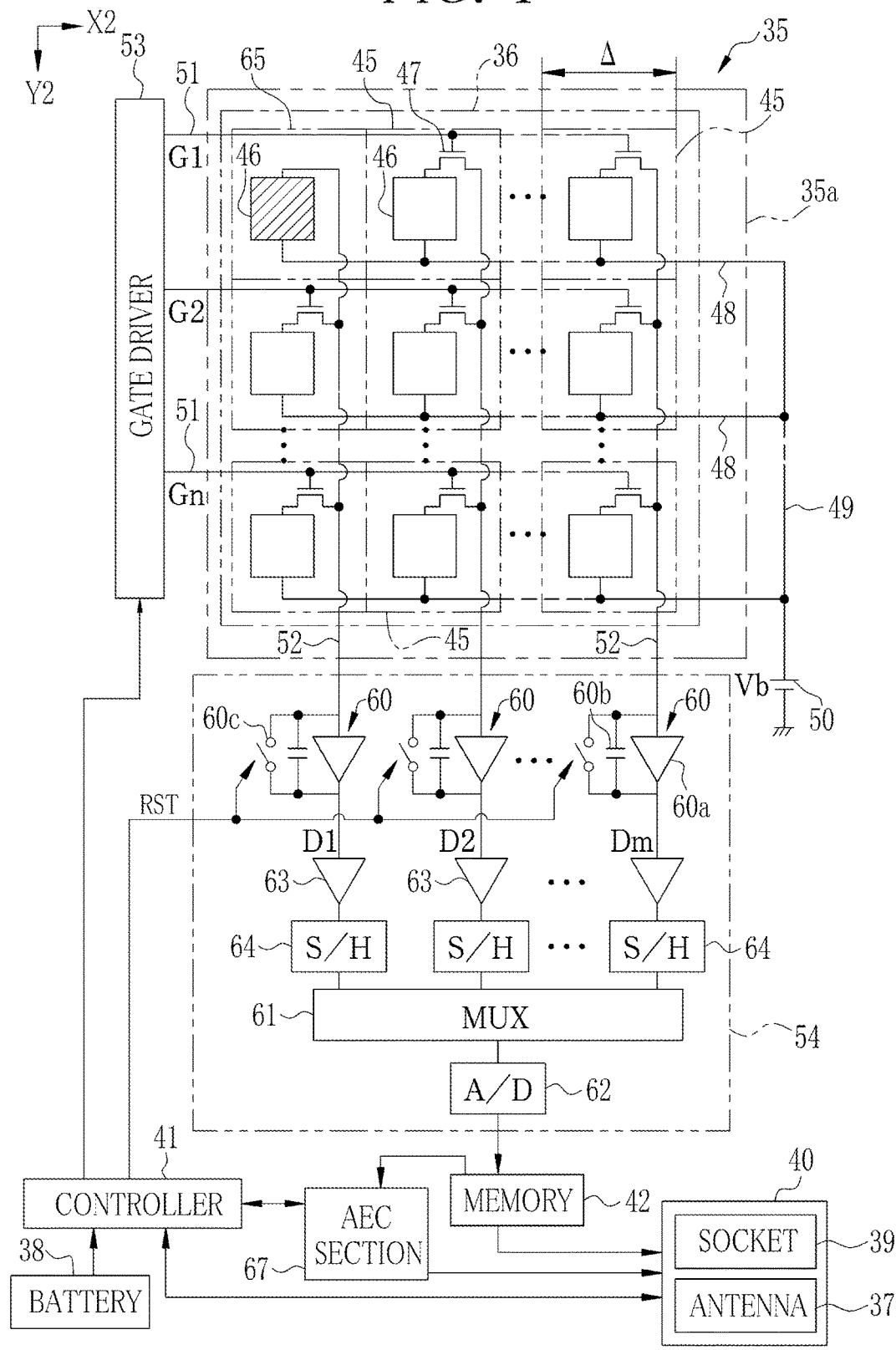
FIG. 4 is a block diagram showing the structure of an electronic cassette.

As shown in FIG. 4, the electronic cassette 16 contains an antenna 37, a battery 38, and the image detector 35 having the detection panel 35*a* in the above-described housing. The electronic cassette 16 wirelessly communicates with the console 17 by using the antenna 37 and the battery 38. The antenna 37 transmits and receives a radio wave for the wireless communication to and from the console 17. The battery 38 supplies the electric power to operate each component of the electronic cassette 16. The battery 38 is of relatively small so as to be contained in the slim electronic cassette 16. The battery 38 can be taken out of the electronic cassette 16 and mounted on a specific cradle for recharging. The battery 38 may be recharged by a wireless power feeder.

The electronic cassette 16 is provided with a socket 39, in addition to the antenna 37. The socket 39 is used for establishing wired communication with the console 17, in such a case where the wireless communication between the electronic cassette 16 and the console 17 is disabled due to a shortage of the battery 38 or the like. Connecting a cable of the console 17 to the socket 39 enables the wired communication with the console 17. At this time, the console 17 may feed the electric power to the electronic cassette 16 through the cable connected to the socket 39.

The antenna 37 and the socket 39 are provided in a communication unit 40. The communication unit 40 mediates the transmission and reception of various types of information and signals including image data among the antenna 37 or the socket 39, a controller 41, and a memory 42.

The image detector 35 is composed of the detection panel 35*a* and circuitry for controlling the operation of the detection panel 35*a*. The detection panel 35*a* includes a TFT (thin film transistor) active matrix substrate and the imaging surface 36 provided on the TFT active matrix substrate. The imaging surface 36 has an array of the plurality of pixels 45 for accumulating signal charge in accordance with the amount of the X-rays incident thereon. The plurality of pixels 45 are arrayed into a matrix of n rows (X2 direction)×m columns (Y2 direction) at a predetermined pitch in two dimensions. The detection panel 35*a* is a square in plane. The size of the imaging surface 36 is 430 mm×430 mm, for example. The pixel number is 2880×2880, for example. The pixel 45 is a square pixel having vertical and horizontal sides of equal length, and has a size of 150 µm×150 µm, for example. The horizontal and the vertical lengths of the pixel 45 correspond to a pixel pitch Δ in the X2 and the Y2 directions, respectively.

The detection panel 35*a* is of an indirect conversion type having a scintillator (phosphor, not shown) for converting the X-rays into visible light. The pixels 45 perform photoelectric conversion of the visible light produced by the scintillator. The scintillator is made of CsI:Tl (thallium activated cesium iodide), GOS ($Gd_2O_2S$:Tb terbium activated gadolinium oxysulfide), or the like, and is opposed to the entire imaging surface 36 having the matrix of pixels 45. The scintillator and the TFT active matrix substrate may adopt either a PSS (penetration side sampling) method or an ISS (irradiation side sampling) method. In the PSS method, the scintillator and the substrate are disposed in this order from an X-ray incident side. In the ISS method, the scintillator and the substrate are disposed in reverse order. Note that, a direct conversion type detection panel, which uses a conversion layer (amorphous selenium or the like) for directly converting the X-rays into the electric charge without using the scintillator, may be used instead.

The pixel 45 is composed of a photodiode 46 being a photoelectric conversion element for producing the electric charge (electron and hole pairs) upon entry of the visible light, and the TFT 47 being a switching element.

The photodiode 46 is composed of a semiconducting layer (of a PIN (p-intrinsic-n) type, for example) for producing the electric charge, and upper and lower electrodes disposed on the top and bottom of the semiconducting layer. The lower electrode of the photodiode 46 is connected to the TFT 47. The upper electrode of the photodiode 46 is connected to a bias line 48. The number of the bias lines 48 coincides with the number of rows (n rows) of the pixels 45 in the imaging surface 36, and all the bias lines 48 are bound into a bus 49. The bus 49 is connected to a bias power source 50. The bias power source 50 applies a bias voltage Vb to the upper electrodes of the photodiodes 46 through the bus 49 and the bias lines 48. Since the application of the bias voltage Vb produces an electric field in the semiconducting layer, the electric charge (electron and hole pairs) produced in the semiconducting layer by the photoelectric conversion is attracted to the upper and lower electrodes, one of which has positive polarity and the other has negative polarity. Thereby, the electric charge is accumulated in the photodiode 46.

A gate electrode of the TFT 47 is connected to a scan line 51. A source electrode of the TFT 47 is connected to a signal line 52. A drain electrode of the TFT 47 is connected to the photodiode 46. The scan lines 51 and the signal lines 52 are routed into a lattice. There are provided the scan lines 51 of a number of the rows (n rows) of the pixels 45 in the imaging surface 36 and the signal lines 52 of a number of the columns (m columns) of the pixels 45. The scan lines 51 are connected to a gate driver 53, and the signal lines 52 are connected to a signal processing circuit 54.

The circuitry for controlling the operation of the detection panel 35a includes the controller 41, the gate driver 53, the signal processing circuit 54, and the like. The controller 41 makes the detection panel 35a carry out an accumulation operation in which the pixels 45 accumulate the signal charge in accordance with the amount of the X-rays incident thereon, a readout (actual reading) operation in which the signal charge is read out from the pixels 45, and a reset (idle reading) operation, by driving the TFTs 47 through the gate driver 53.

In the accumulation operation, while the TFTs 47 are turned off, the pixels 45 accumulate the signal charge. In the readout operation, the gate driver 53 sequentially issues gate pulses G1 to Gn to drive the TFTs 47 of the same row at a time. Thereby, the scan lines 51 are activated one by one to turn on the TFTs 47 connected to the activated scan line 51 on a row-by-row basis. The duration of turn-on is defined by a pulse width of the gate pulse, and the TFT 47 is returned to a turn-off state after a lapse of time defined by the pulse width. Upon turning on the TFT 47, the electric charge accumulated in the photodiode 46 of the pixel 45 is read out to the signal line 52, and inputted to the signal processing circuit 54.

The signal processing circuit 54 includes integrating amplifiers 60, a multiplexer (MUX) 61, an A/D converter (A/D) 62, and the like. The integrating amplifier 60 is connected to each signal line 52 on a one-by-one basis. The integrating amplifier 60 is composed of an operational amplifier 60a and a capacitor 60b connected between input and output terminals of the operational amplifier 60a. The signal line 52 is connected to one of the input terminals of the operation amplifier 60a. The other input terminal of the operational amplifier 60a is connected to a ground (GND). A reset switch 60c is connected in parallel with the capacitor 60b. The integrating amplifier 60 integrates the electric charge inputted from the signal line 52. The integrating amplifiers 60 convert the electric charge into voltage signals D1 to Dm, and output the voltage signals D1 to Dm. To the output terminal of the operational amplifier 60a of each column, the MUX 61 is connected through another amplifier 63 and a sample-hold (S/H) circuit 64. The A/D converter 62 is connected to an output of the MUX 61.

The MUX 61 sequentially selects one of the plurality of integrating amplifiers 60 connected in parallel, and inputs the voltage signals D1 to Dm outputted from the selected integrating amplifiers 60 in series to the A/D converter 62. The A/D converter 62 converts the inputted voltage signals D1 to Dm into digital data, and outputs the digital data to the memory 42 contained in the electronic cassette 16. Another amplifier may be connected between the MUX 61 and the A/D converter 62.

After the MUX 61 reads out the voltage signals D1 to Dm of one row from the integrating amplifiers 60, the controller 41 outputs a reset pulse RST to the integrating amplifiers 60 to turn on the reset switches 60c. Thereby, the signal charge of one row accumulated in the capacitors 60b is discharged and reset. Upon the reset of the integrating amplifiers 60, the gate driver 53 outputs the gate pulse of the next row to start reading out the signal charge from the pixels 45 of the next row. By sequential repetition of this operation, the signal charge is read out from the pixels 45 of every row.

After the completion of the readout from every row, the image data representing the X-ray image of one frame is stored to the memory 42. This image data is read out of the memory 42, and outputted to the console 17 through the communication unit 40. Thereby, the X-ray image of the patient is detected.

Dark charge occurs in the semiconducting layer of the photodiode 46 irrespective of the presence or absence of entry of the X-rays. Due to the application of the bias voltage Vb, the dark charge is accumulated in the photodiode 46 of the pixel 45. The dark charge occurring in the pixels 45 becomes a noise component of the image data, and therefore the reset operation is carried out to remove this. The reset operation is an operation in which the dark charge produced in the pixels 45 is discharged through the signal lines 52.

The reset operation adopts a sequential reset method, for example, by which the pixels 45 are reset on a row-by-row basis. In the sequential reset method, just as with the readout operation of the signal charge, the gate driver 53 sequentially issues the gate pulses G1 to Gn to the scan lines 51 to turn on the TFTs 47 of the pixels 45 on a row-by-row basis. While the TFT 47 is turned on, the dark charge flows from the pixel 45 through the signal line 52 into the capacitor 60b of the integrating amplifier 60. In the reset operation, in contrast to the readout operation, the MUX 61 does not read out the electric charge accumulated in the capacitors 60b. In synchronization with the issue of each of the gate pulses G1 to Gn, the controller 41 outputs the reset pulse RST to turn on the reset switches 60c. Thereby, the electric charge accumulated in the capacitors 60b is discharged, and the integrating amplifiers 60 are reset.

Instead of the sequential reset method, a parallel reset method or all pixels reset method may be used. In the parallel reset method, a plurality of rows of pixels are grouped together, and sequential reset is carried out in each group, so as to concurrently discharge the dark charge from the rows of the number of the groups. In the all pixels reset method, the gate pulse is inputted to every row to discharge the dark charge from every pixel at a time. Adoption of the parallel reset method and the all pixels reset method allows speeding up the reset operation.

Upon receiving the emission start request signal from the controller 21 of the source control device 14, the controller 41 makes the detection panel 35a carry out the reset operation, and sends the emission permission signal back to the source control device 14. After that, upon receiving the emission start signal, the controller 41 shifts the operation of the detection panel 35a from the reset operation to the accumulation operation.

The detection panel 35a is provided with a plurality of detection pixels 65 connected to the signal lines 52 in a short manner without passing through the TFTs 47, besides the normal pixels 45 connected to the signal lines 52 through the TFTs 47 as described above, in the same imaging surface 36. The detection pixel 65 functions as a dose detection sensor for detecting the dose of the X-rays incident upon the imaging surface 36 through the patient M. In this embodiment, one detection pixel 65 composes one dose detection sensor. The detection pixels 65 occupy an order of several % of the pixels 45 in the imaging surface 36. In the detection pixel 65 according to this embodiment, the photodiode 46 and the like have exactly the same fundamental structure as those of the pixel 45. Therefore, the detection pixels 65 and the pixels 45 can be formed in approximately the same manufacturing process. Accordingly, the size of one detection pixel 65 is 150 µm×150 µm, just as with the size of the pixel 45.

Since the detection pixel 65 is connected to the signal line 52 directly without passing through the TFT 47, the signal charge produced in the detection pixel 65 immediately flows into the signal line 52, irrespective of the turn on and off of the TFT 47. The same goes if the normal pixels 45 in the same row have the TFTs 47 turned off and are in the accumulation operation for accumulating the signal charge. Thus, the electric charge produced in the photodiode 46 of the detection pixel 65 always flows into the capacitor 60b of the integrating amplifier 60 in the signal line 52 connected to the detection pixel 65. During the accumulation operation of the detection panel 35a, the electric charge from the detection pixel 65 is accumulated in the capacitor 60b, and outputted through the MUX 61 to the A/D converter 62 as a voltage value at a predetermined sampling period. The A/D converter 62 outputs the voltage value to the memory 42 as a dose detection signal of each detection pixel 65. The dose detection signal represents the dose of the X-rays applied per unit of time. The dose detection signal outputted at the predetermined sampling period is sequentially outputted to the memory 42.

Figure 5:
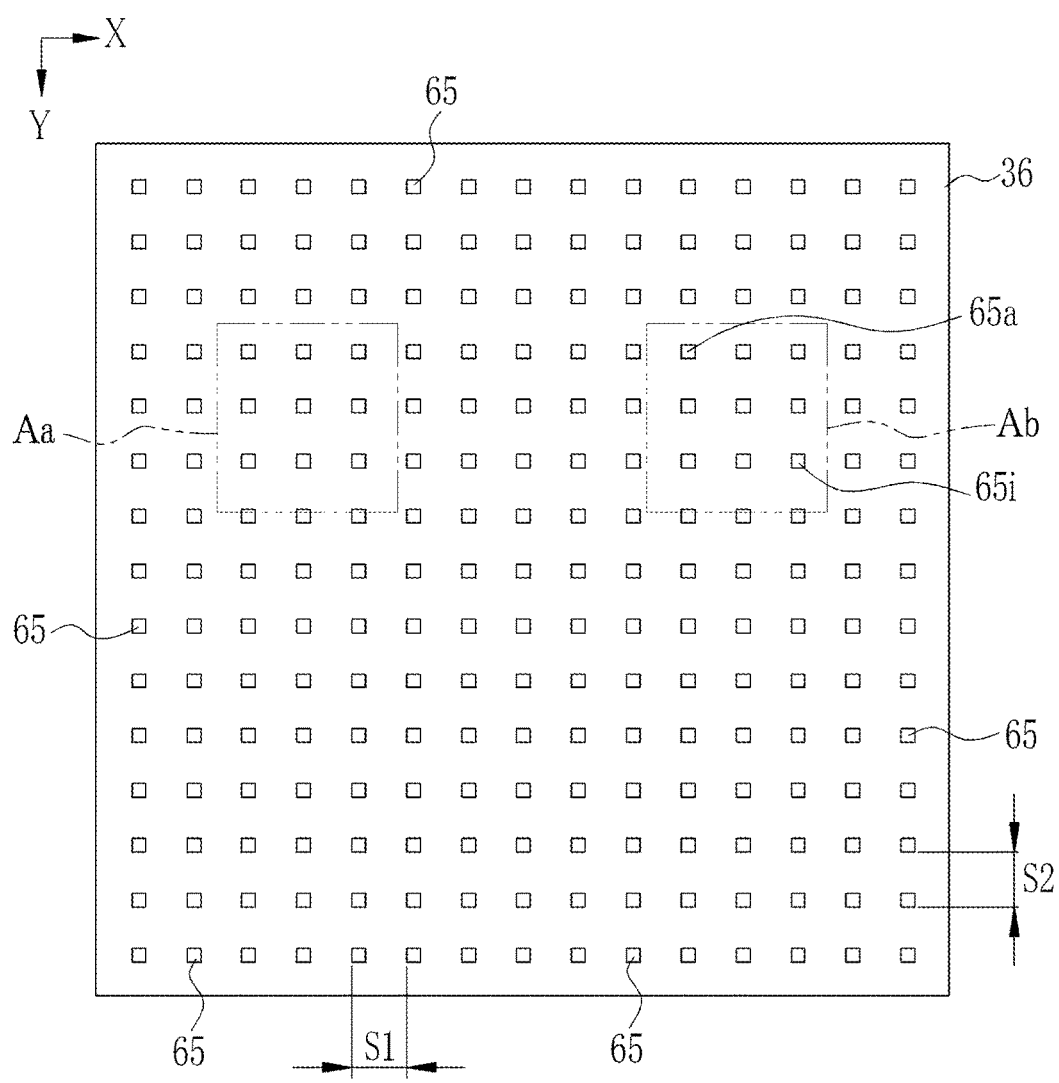
FIG. 5 is a diagram explaining the disposition of detection pixels and measurement areas in a detection panel of the electronic cassette.

As shown in FIG. 5, the detection pixels 65 are arrayed at constant arrangement periods S1 and S2 in the X2 and Y2 directions so as to be uniformly distributed over the imaging surface 36, without being localized in the imaging surface 36. The positions of the detection pixels 65 are already known in manufacturing the detection panel 35a, and an internal memory (not shown) of the controller 41 stores in advance coordinate information representing the position of each detection pixel 65 in the imaging surface 36. The dose detection signal of each detection pixel 65 outputted from the A/D converter 62 is recorded to the memory 42 in correspondence with the coordinate information.

The operation of an AEC section (automatic exposure control section) 67 is controlled by the controller 41. The AEC section 67 reads out the dose detection signal of each detection pixel 65 from the memory 42, and carries out AEC based on the read dose detection signal.

Figure 6:
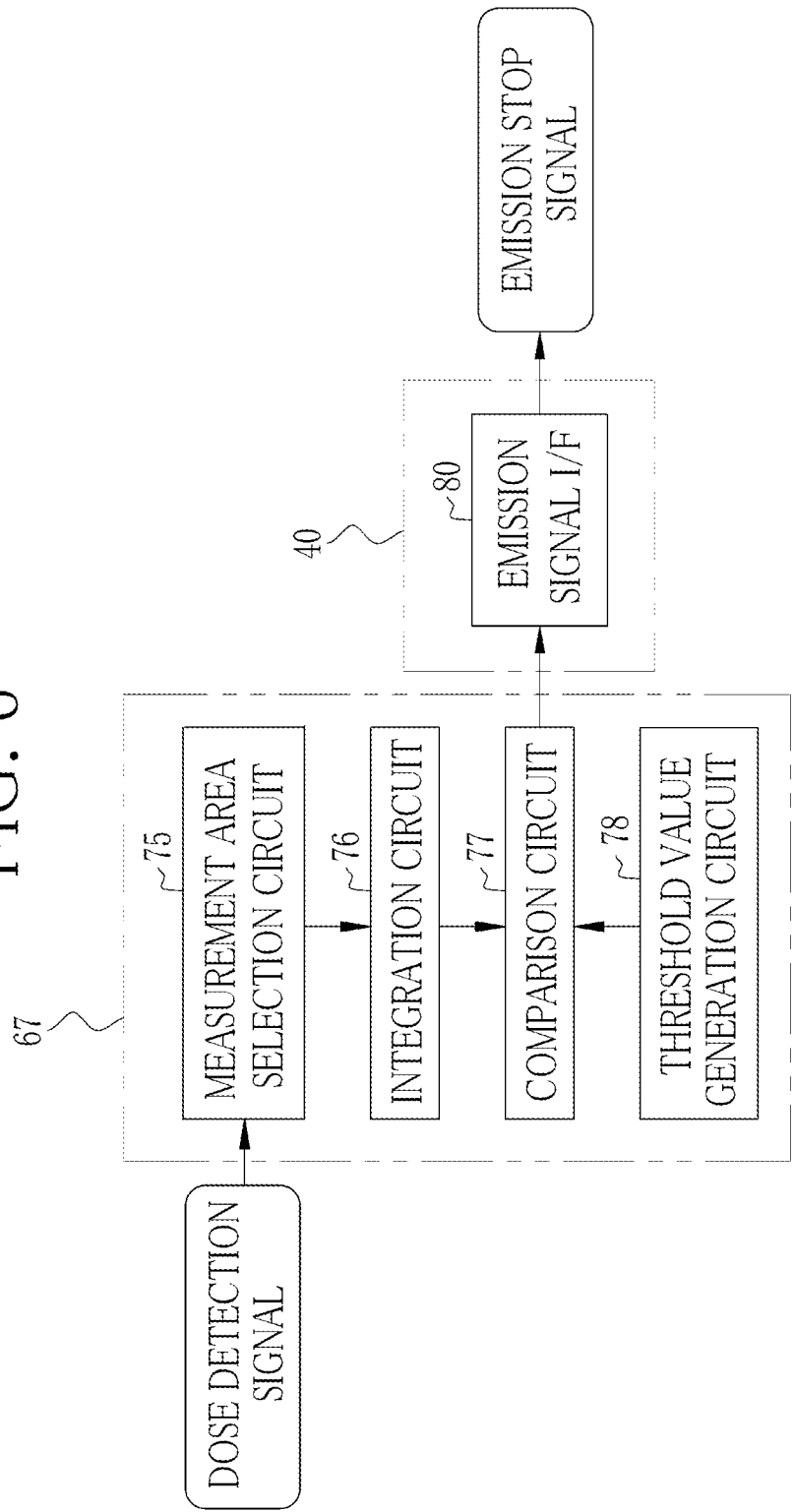
FIG. 6 is a block diagram showing the structure of an AEC section of the electronic cassette.

As shown in FIG. 6, the AEC section 67 has a measurement area selection circuit 75, an integration circuit 76, a comparison circuit 77, and a threshold value generation circuit 78. The measurement area selection circuit 75 chooses one or more of the plurality of detection pixels 65 distributed over the imaging surface 36 whose dose detection signals are to be used in the AEC, based on the information of a measurement area set in the imaging condition. The integration circuit 76 calculates an average of the outputted values of the dose detection signals from the detection pixels 65 chosen by the measurement area selection circuit 75. For example, in a case where areas Aa and Ab represented by chain double-dashed lines in FIG. 5 are chosen as the measurement areas, the integration circuit 76 calculates an average of output values of dose detection signals of nine detection pixels 65a to 65i in each of the measurement areas Aa and Ab. Otherwise, the integration circuit 76 calculates an average of output values of eighteen detection pixels 65 in total in the measurement areas Aa and Ab. The average is calculated whenever the dose detection signals are sampled. Then, the integration circuit 76 obtains an integral value by integrating the average. The integral value represents the integral dose of the applied X-rays. The comparison circuit 77 compares the integral value of the dose detection signals from the integration circuit 76 with an emission stop threshold value applied from the threshold value generation circuit 78. Upon the integral value reaching the threshold value, the comparison circuit 77 outputs the emission stop signal.

The communication unit 40 is provided with an emission signal I/F 80, in addition to the antenna 37 and the socket 39 described above. To the emission signal I/F 80, the emission signal I/F 25 of the source control device 14 is connected. The emission signal I/F 80 performs reception of the emission start request signal, transmission of the emission permission signal in response to the emission start request signal, reception of the emission start signal, and transmission of the emission stop signal outputted from the comparison circuit 77.

Figure 7:
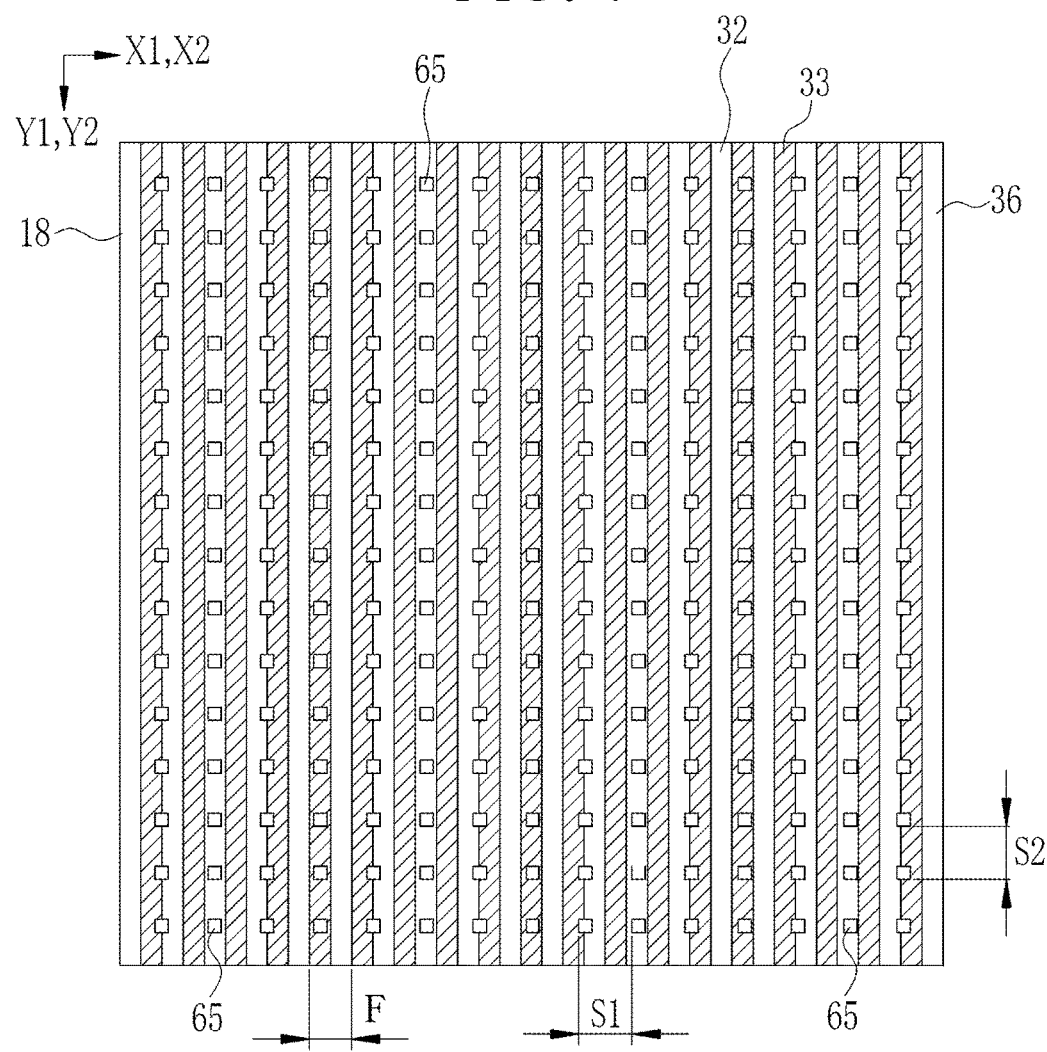
FIG. 7 is an explanatory view showing an arrangement of the detection pixels in a state of overlaying the grid on an imaging surface of the detection panel.

As shown in FIG. 7, in grid imaging using the grid 18, the grid 18 is disposed in front (on the X-ray incident side) of the imaging surface 36, so that the grid 18 is overlaid on the detection pixels 65. The arrangement period S1 of the detection pixels 65 in the X2 direction is different from the arrangement period F of the X-ray absorbing portions 33 of the grid 18 (S1≠F). Also, the arrangement period S1 of the detection pixels 65 is not an integral multiple of the arrangement period F of the X-ray absorbing portions 33. In other words, "arrangement period S1≠N·arrangement period F" (N is an integer) holds true.

Figure 8:
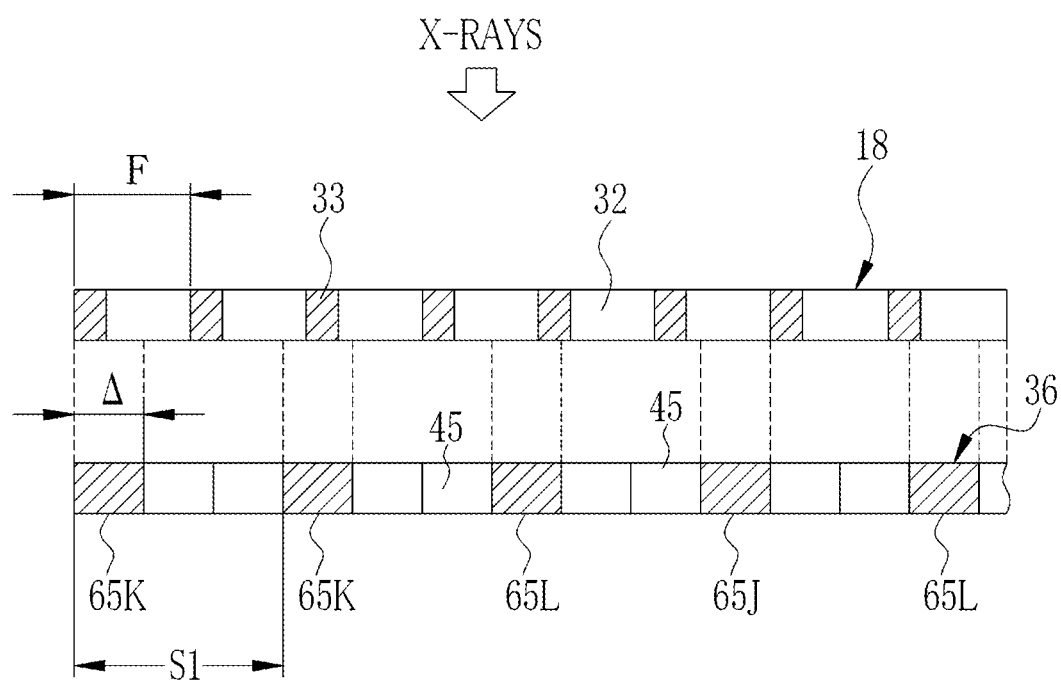
FIG. 8 is an explanatory view showing the relation between an arrangement period of the detection pixels and a grid pitch.

In this embodiment, as shown in FIG. 8, the detection pixels 65 are arranged every three pixels with leaving space of two pixels 45 between the two detection pixels 65. In the case of arranging the detection pixels 65 every three pixels, the arrangement period S1 of the detection pixels 65 has a length of three pixels. Since the pixel pitch Δ=150 µm, the arrangement period S1 is 150 µm×3=450 µm. On the other hand, since the grid density of the grid 18 is 4/mm in this embodiment, the arrangement period F is 250 µm. Accordingly, the arrangement period S1 (450 µm) does not coincide with the arrangement period F (250 µm). Also, dividing the arrangement period S1 by the arrangement period F results in 450/250=1.8, so the arrangement period S1 is not an integral multiple of the arrangement period F.

As described above, since "arrangement period S1≠N·arrangement period F" (N is an integer) holds true, as shown in FIG. 8, not all the detection pixels 65 are disposed behind the X-ray transmitting portions 32 or the X-ray absorbing portions 33. There are a detection pixel 65J situated behind the X-ray transmitting portion 32, a detection pixel 65K situated behind the entire X-ray absorbing portion 33, and a detection pixel 65L situated behind a part, not entire, of the X-ray absorbing portion 33. Therefore, not all of the plurality of detection pixels 65 has maximum output values or minimum output values.

Taking FIG. 8 as an example, the dose detection signal of the detection pixel 65J has a maximum output value, and the dose detection signal of the detection pixel 65K has a minimum output value. The dose detection signal of the detection pixel 65L takes an output value between the maximum output value and the minimum output value.

Figure 9:
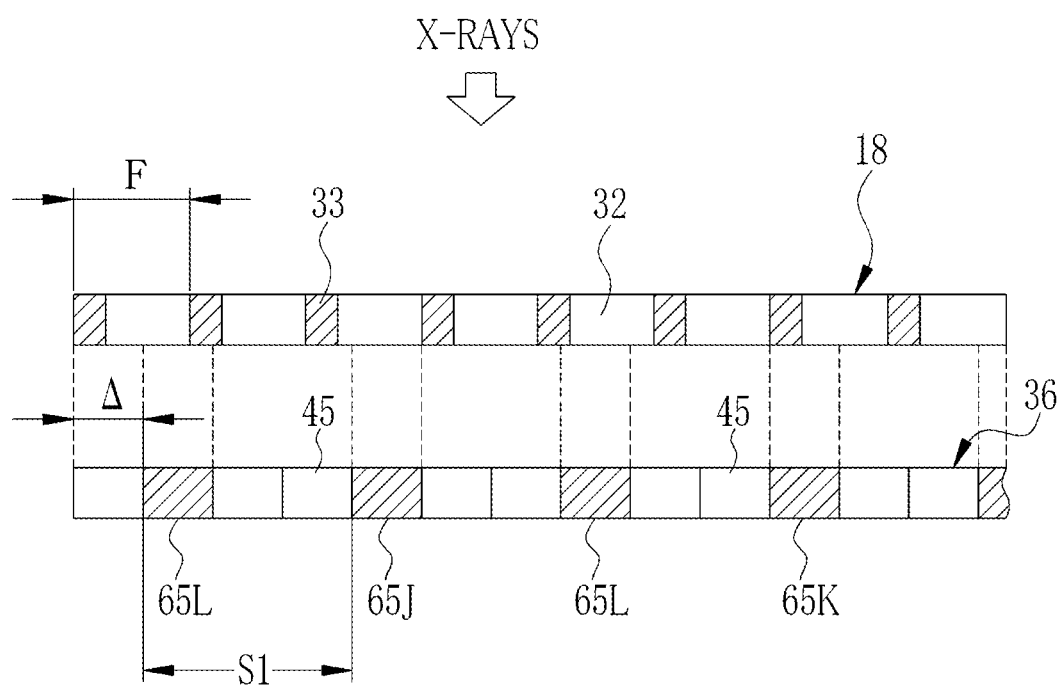
FIG. 9 is an explanatory view showing positional variation of the detection pixels and the grid by a shift of one pixel from the state of FIG. 8.

As described above, the output value of the dose detection signal of each detection pixel 65 is distributed within the confines between the maximum output value and the minimum output value. Also, as shown in FIG. 9, if the geometrical disposition between the grid 18 and the detection pixels 65 is shifted from a state shown in FIG. 8 by a size of one pixel 45 due to an attachment backlash or a manufacturing error of the grid 18, the detection pixels 65J to 65L exist. Thus, the output value of each detection pixel 65 is distributed in the confines between the maximum output value and the minimum output value. Also in this case, not all the detection pixels 65 have the maximum output values or the minimum output values.

Since the output values of the plurality of detection pixels 65 are distributed in the confines between the maximum output value and the minimum output value, a variation range of the average of the output values is smaller than the difference between the maximum output value and the minimum output value. As described above, the AEC section 67 uses the average of the output values of the detection pixels 65 in the measurement areas Aa and Ab shown in FIG. 5 for judgment of the AEC. Reduction in the variation range of the average translates into stability of the output value in accordance with the dose incident upon the measurement areas Aa and Ab, even in a case where the geometrical disposition between the grid 18 and the detection pixels 65 is misaligned. Therefore, the stable AEC can be carried out without being affected by misalignment in the geometrical disposition between the grid 18 and the detection pixels 65.

On the other hand, in a comparative example shown in FIGS. 10 and 11, an arrangement period S1a=the arrangement period F holds true. In this case, the variation range of the output value of each detection pixel 65 is a maximum output difference being the difference between the maximum output value and the minimum output value. In FIGS. 10 and 11, a letter symbol Δa represents a pixel pitch of the pixels 45. The detection pixels 65 are disposed every other pixel, and the arrangement period S1a of the detection pixels 65 is a length of the two pixels 45. FIG. 11 shows a case in which the geometrical disposition between the grid 18 and the detection pixels 65 is shifted from a state shown in FIG. 10 by a length of one pixel 45.

If the arrangement period S1a=the arrangement period F, there are cases in which only the detection pixels 65K are present each of which is disposed behind the entire X-ray absorbing portion 33 as shown in FIG. 10, or only the detection pixels 65J are present each of which is disposed behind the X-ray transmitting portion 32 as shown in FIG. 11. Thus, the output value of each detection pixel 65 is not distributed, and every detection pixel 65 has the same output value. Only the detection pixels 65K are present in FIG. 10, so every detection pixel 65 outputs the minimum output value. Only the detection pixels 65J are present in FIG. 11, on the contrary, so every detection pixel 65 outputs the maximum output value. A shift of the geometrical disposition between the grid 18 and the detection pixels 65 by a length of just one pixel 45 varies the output value of each detection pixel 65 from the minimum output value to the maximum output value. In the comparative example, since every detection pixel 65 takes the same output value, the average of the output values of the detection pixels 65 is equal to the output value of the one detection pixel 65. Accordingly, the variation range of the average is the maximum output difference, being the difference between the maximum output value and the minimum output value. The large variation range of the average hinders the stable AEC, because the misalignment in the geometrical disposition between the grid 18 and the detection pixels 65 affects severely.

FIG. 12 shows a comparative example in which the arrangement period S1a of FIGS. 10 and 11 is modified to a length three times as large as the arrangement period F (S1a=F×3). Also in a case where the arrangement period S1a is an integral multiple of the arrangement period F, just as with FIGS. 10 and 11, the detection pixels 65 are unified into one type of the detection pixels 65J to 65L (detection pixels 65K are shown as an example in FIG. 12), and the plurality of detection pixels 65 has the same output values. Therefore, just as with the comparative example shown in FIGS. 10 and 11, the variation range of the output value of each detection pixel 65 is the maximum output difference, and hence the stable AEC cannot be carried out.

Figure 13:
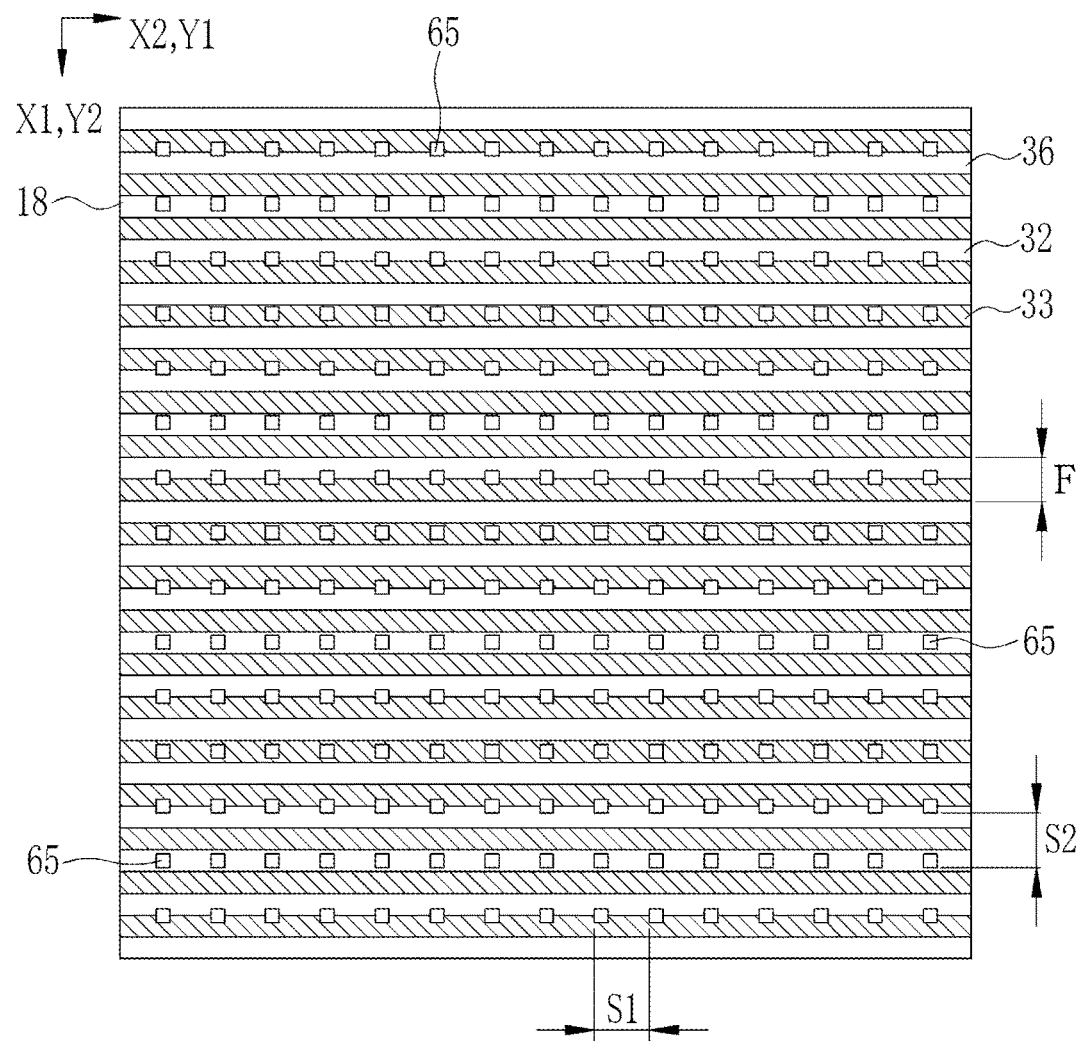
FIG. 13 is an explanatory view showing an arrangement of the detection pixels in a state of overlaying the grid turned 90° on the imaging surface of the detection panel.

The pixel 45 is a square pixel, and the pixel pitch of the pixels 45 in the Y2 direction is A, which is the same as the pixel pitch in the X2 direction. The arrangement period S2 of the detection pixels 65 in the Y2 direction is the same as the arrangement period S1. Therefore, in a case where the arrangement period S1 is different from the arrangement period F and not an integral multiple of the arrangement period F, the arrangement period S2 is different from the arrangement period F too and not an integral multiple of the arrangement period F neither. In other words, as for the arrangement period S2, "the arrangement period S2≠N·arrangement period F" (N is an integer) holds true just as with the arrangement period S1. Thus, as shown in FIG. 13, in the case of using the grid 18 in a state of being turned 90° from a state shown in FIG. 7, the average of the output values of the plurality of detection pixels 65 has a smaller variation range (smaller than the maximum output difference), as compared with the comparative examples shown in FIGS. 9 to 11, so that the stable AEC can be carried out.

Figure 14:
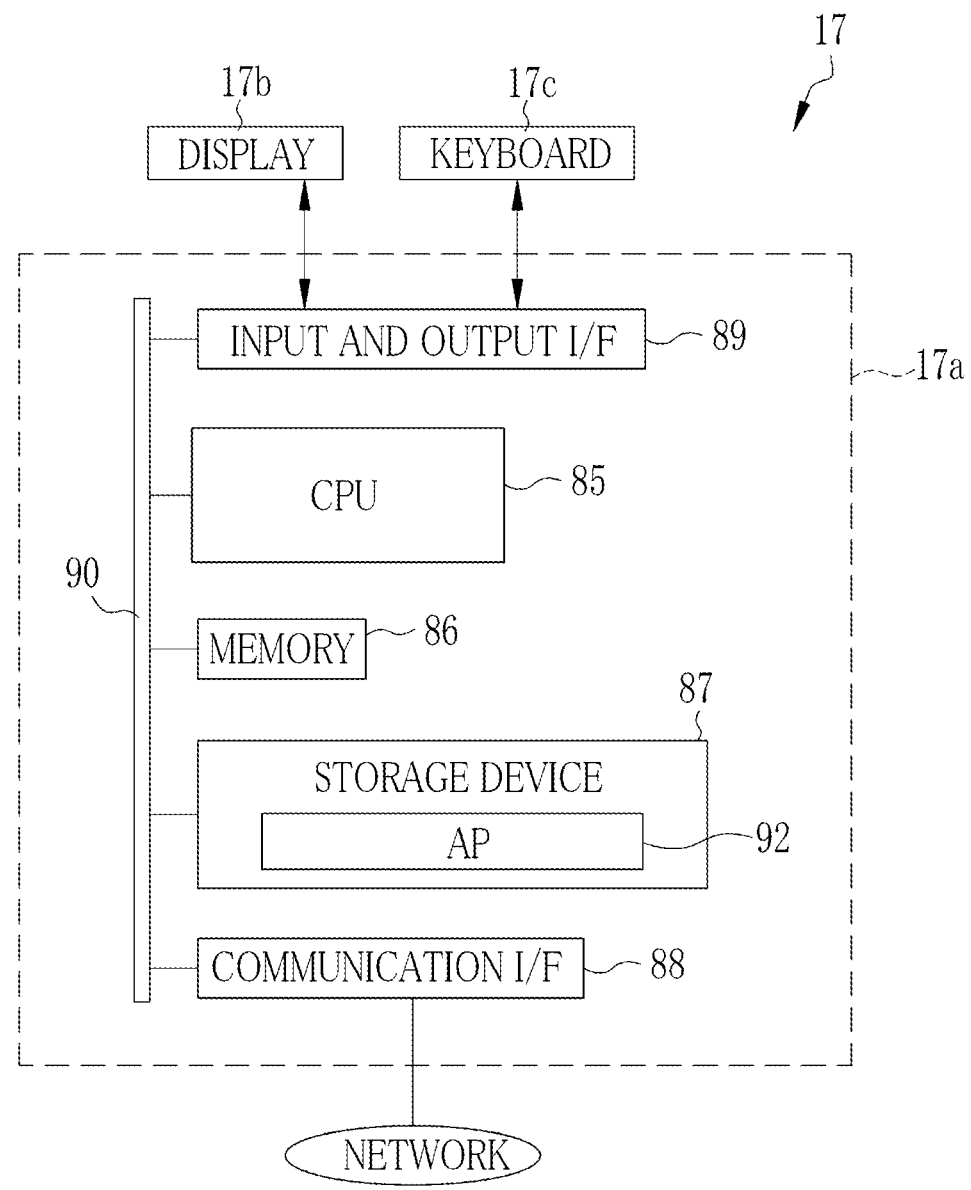
FIG. 14 is a block diagram showing the internal structure of a console.

As shown in FIG. 14, the console 17 is composed of a console body 17a, a display 17b, and a keyboard 17c. The console 17 is wiredly or wirelessly connected to the electronic cassette 16 in a communicatable manner, and controls the operation of the electronic cassette 16. To be more specific, the console 17 not only transmits the imaging condition to the electronic cassette 16 to set conditions (gain of the amplifier for amplifying a voltage corresponding to the accumulated signal charge, and the like) for the AEC and signal processing of the signal processing circuit 54, but also controls the turn on and off of the electronic cassette 16, mode switching to a power saving mode or an imaging ready state, and the like.

The console 17 applies various types of image processing such as an offset correction, a gain correction, and a defect correction to the X-ray image data transmitted from the electronic cassette 16. In the defect correction, pixel values of the column having the detection pixel 65 are interpolated with pixel values of the adjoining columns without having the detection pixel 65. The X-ray image after being subjected to the image processing is displayed on the display 17b, and its data is recorded to data storage such as a storage device 87 or a memory 86 contained in the console body 17a, or an image storage server connected to the console 17 through a network. Note that, the electronic cassette 16 may perform each type of the above-described image processing.

The console 17 receives an input of an examination order, which includes information about the sex and the age of a patient, a body part to be imaged, and a purpose of imaging, and displays the examination order on the display 17b. The examination order is inputted from an external system, e.g. an HIS (hospital information system) or an RIS (radiography information system), that manages patient data and examination data related to radiography, or inputted manually by the operator. The examination order includes the body part to be imaged e.g. head, chest, abdomen, or the like, and an imaging direction e.g. anterior, medial, diagonal, PA (X-rays are applied from a posterior direction), or AP (X-rays are applied from an anterior direction). The operator confirms the contents of the examination order on the display 17b, and inputs the imaging condition corresponding to the contents through an operation screen of the console 17.

As shown in FIG. 15, imaging conditions, which are different from one body part to another, can be set in the console 17. The imaging condition includes the tube voltage, the tube current, the measurement area of the detection pixels 65, the emission stop threshold value used for comparison with the integral value of the dose detection signals of the detection pixels 65 to judge the stop of the X-ray emission, and the like. This information about the imaging conditions is stored to the storage device 87. The same imaging condition is set manually by the operator to the source control device 14 with referring to the imaging condition of the console 17.

The measurement area, which represents an area of the detection pixels 65 to be used in the AEC, corresponds to a region of interest to be most noticed in a diagnosis in each body part, and is set at an area from which the dose detection signals are stably obtained. In a case where the body part to be imaged is a chest, for example, portions of lung fields are assigned as the measurement areas, shown as the measurement areas Aa and Ab enclosed by the chain double-dashed lines in FIG. 5. The measurement area is represented by X and Y coordinates. In the case of a rectangular measurement area, like this embodiment, the X and Y coordinates of two points connected by a diagonal line are stored. The X and Y coordinates correspond to the positions of the pixels 45 (including the detection pixels 65) in the imaging surface 36 of the electronic cassette 16. The X and Y coordinates are represented under the condition that an X axis extends in a direction parallel to the scan lines 51, and a Y axis extends in a direction parallel to the signal lines 52, and the coordinates of the most upper left pixel 45 are assigned as an origin point (0, 0).

As shown in FIG. 14, the console body 17a is provided with a CPU 85, the memory 86, the storage device 87, a communication I/F 88, and an input and output I/F 89. These components are connected each other through a data bus 90. The display 17b and the keyboard 17c are connected to the console body 17a through the input and output I/F 89. Note that, a mouse, a touch panel, and the like may be used instead of the keyboard 17c.

The storage device 87 is a hard disk drive (HDD), for example. The storage device 87 stores a control program and an application program (hereinafter called AP) 92. The AP 92 is a program that makes the console 17 perform various functions related to radiography, such as display processing of the examination order and the X-ray image, image processing of the X-ray image, and a setup of the imaging condition.

The memory 86 is a work memory that the CPU 85 uses in executing processing. The CPU 85 loads the control program stored on the storage device 87 into the memory 86, and runs the program for centralized control of each part of a computer. The communication I/F 88 is a network interface for performing wireless or wired transmission control from/to an external device such as the RIS, the HIS, the image storage server, and the electronic cassette 16.

Figure 16:
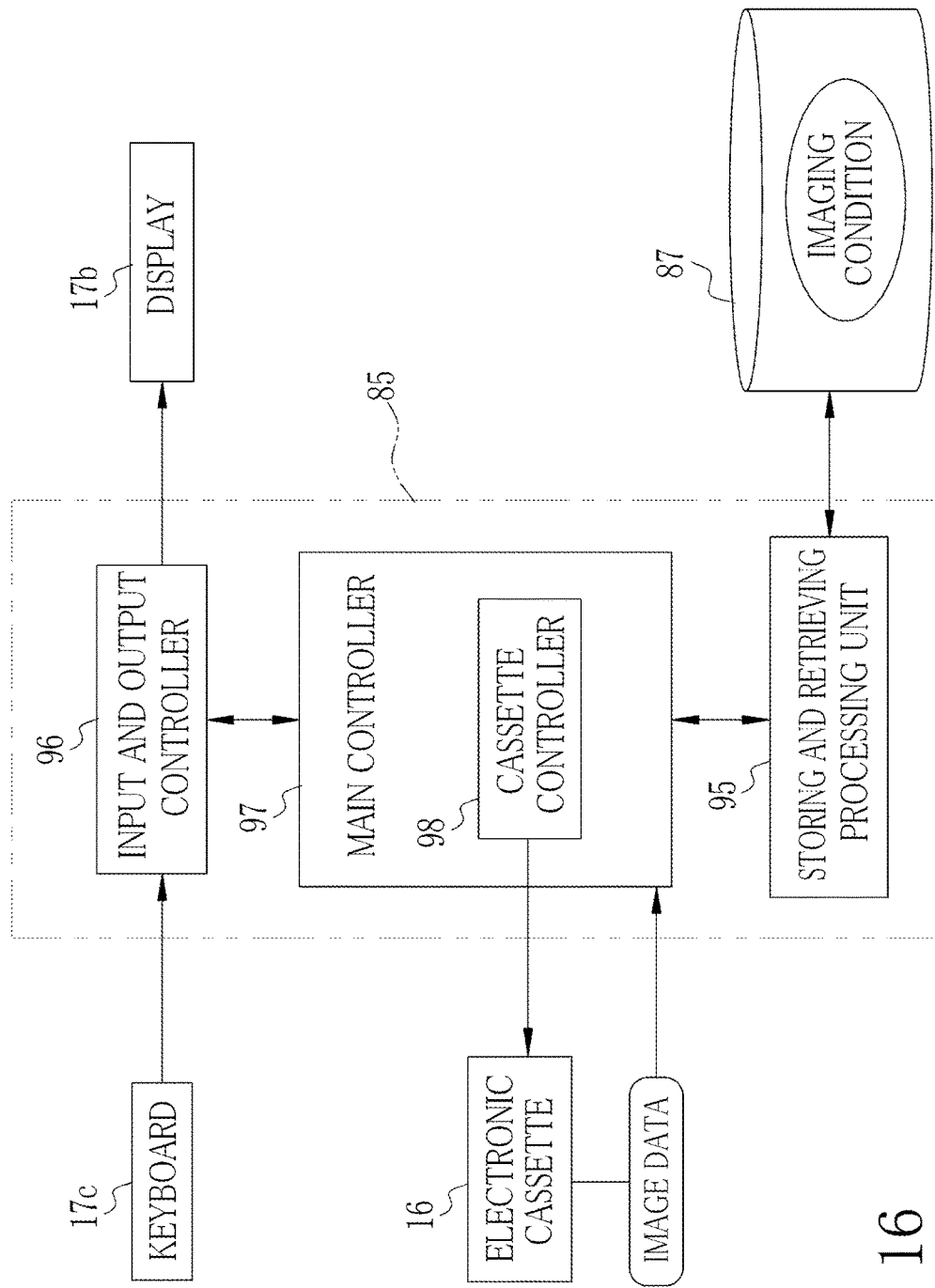
FIG. 16 is a block diagram showing the functions of the console.

As shown in FIG. 16, by running the AP 92, the CPU 85 of the console 17 functions as a storing and retrieving processing unit 95, an input and output controller 96, and a main controller 97. The storing and retrieving processing unit 95 performs storing processing of various types of data to the storage device 87, and retrieval processing from the various types of data stored in the storage device 87. The input and output controller 96 reads out drawing data corresponding to an operation on the keyboard 17c from the storage device 87 through the input and output I/F 89, and outputs to the display 17b various types of operation screens of GUIs based on the read drawing data. The input and output controller 96 receives input of operation commands from the keyboard 17c through the operation screens. The main controller 97 includes a cassette controller 98 for controlling the operation of the electronic cassette 16, and performs centralized control of the operation of each part of the console 17. The cassette controller 98 receives the information about the measurement area and the information about the emission stop threshold value according to the imaging condition from the storing and retrieving processing unit 95, and supplies the electronic cassette 16 with the information.

Note that, in the console 17, an image processor for performing various types of imaging processing such as the offset correction, the gain correction, and the defect correction described above and a communicator for mediating communication with the source control device 14 and the electronic cassette 16 are established in the CPU 85, in addition to the components described above. Note that, each component may be established by specific hardware, instead of actualizing the function of each component by software, as with this embodiment. The electronic cassette 16 may perform all or a part of the image processing including the offset correction, the gain correction, the defect correction, and the like.

Figure 17:
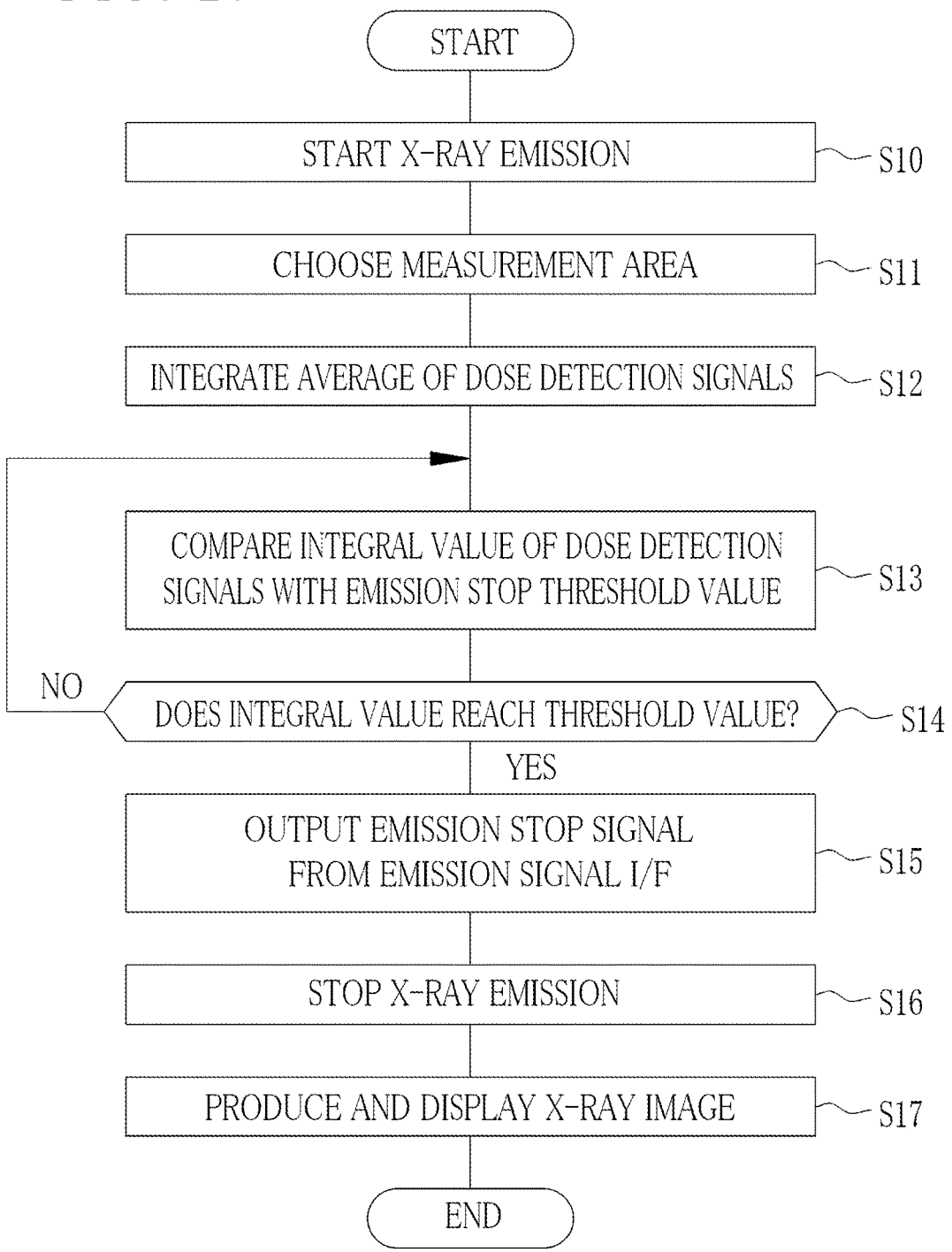
FIG. 17 is a flowchart showing a procedure of X-ray imaging.

Next, an X-ray imaging procedure by the X-ray imaging system 10 will be described with referring to a flowchart of FIG. 17.

Firstly, while the patient M stands in a predetermined position in front of the imaging stand 30, the height and the horizontal position of the electronic cassette 16 set in the imaging stand 30 are adjusted for positioning with the patient's body part to be imaged. In accordance with the position of the electronic cassette 16 and the size of the body part to be imaged, the height and the horizontal position of the X-ray source 13 and the size of the irradiation field are adjusted. Then, the electronic cassette 16 is turned on. The imaging condition is inputted with the keyboard 17c. The imaging condition and the measurement area, the emission stop threshold value, and the like according to the imaging condition are outputted through the cassette controller 98 to the electronic cassette 16. In a like manner, the imaging condition is also set in the source control device 14.

After the completion of preparation for imaging, the operator performs the first-step push of the emission switch 15. Thereby, the warm-up start signal is transmitted to the source control device 14 to start warming up the X-ray source 13. After a lapse of predetermined time, upon the second-step push of the emission switch 15, the emission start signal is transmitted to the source control device 14 to start the X-ray emission (S10). The X-rays radiating from the X-ray source 13 produces the scattered radiation in passing through the patient M. This scattered radiation is removed by the grid 18.

Before the start of the X-ray emission, the detection panel 35a carries out the reset operation. Upon receiving the emission start signal from the source control device 14, the reset operation is shifted to the accumulation operation.

In parallel with the accumulation operation of the detection panel 35a, the AEC section 67 performs the AEC based on the dose detection signals of the detection pixels 65 in the electronic cassette 16. The measurement area selection circuit 75 chooses the dose detection signals outputted from the detection pixels 65 existing in the measurement areas based on the information about the measurement areas supplied by the console 17, out of the dose detection signals of the plurality of detection pixels 65 inputted from the A/D converter 62, and outputs the chosen dose detection signals to the integration circuit 76 (S11). The integration circuit 76 integrates the average of the output values of the dose detection signals.

The relation between the arrangement period S1 of the detection pixels 65 in the X2 direction and the arrangement period F and between the arrangement period S2 of the detection pixels 65 in the Y2 direction and the arrangement period F satisfies "arrangement period S1, S2≠N·arrangement period F" (N is an integer). Thus, the output value of the dose detection signal of each detection pixel 65 is distributed. Accordingly, if the geometrical disposition between the grid 18 and the detection pixels 65 is misaligned, the average of the output values of the detection pixels 65 has the small variation range, and therefore the stable AEC can be carried out without being affected by the geometrical disposition between the grid and the detection pixels 65.

The threshold value generation circuit 78 produces the emission stop threshold value provided by the cassette controller 98, and outputs the emission stop threshold value to the comparison circuit 77. The comparison circuit 77 compares the integral value of the dose detection signals integrated by the integration circuit 76 with the emission stop threshold value (S13). In a case where the integral value reaches the emission stop threshold value (YES in S14), the emission stop signal is outputted. The emission stop signal outputted from the comparison circuit 77 is transmitted through the emission signal I/F 80 to the emission signal I/F 25 of the source control device 14 (S15).

Upon receiving the emission stop signal by the emission signal I/F 25, the controller 21 stops the electric power supply from the high voltage generator 20 to the X-ray source 13 in the source control device 14, and therefore the X-ray emission is stopped (S16). At the instant when an emission stop detecting circuit of the AEC section 67 detects the stop of the X-ray emission, the detection panel 35a stops the accumulation operation and shifts to the readout operation, so that the X-ray image is outputted to the memory 42. After the readout operation, the detection panel 35a restarts the reset operation.

The X-ray image is transmitted through the communication unit 40 to the console 17. The X-ray image is subjected to the various types of image processing, and displayed on the display 17b by the input and output controller 96 (S17).

According to the present invention, the variation range of the output value of the detection pixel 65 is reduced by determining the arrangement periods S1 and S2 of the detection pixels 65 in relation to the arrangement period F of the grid 18. Therefore, in contrast to the U.S. Pat. No. 6,944,266, it is not necessary to obtain the gain image whenever the imaging is performed, and correct the output value of each detection pixel based on the obtained gain image. In the case of the U.S. Pat. No. 6,944,266, if the geometrical disposition between the grid 18 and the detection pixels 65 is misaligned by an impact or the like after the obtainment of the gain image, the AEC cannot be performed appropriately due to an improper correction of the output values. However, according to the present invention, the AEC can be appropriately carried out if the geometrical disposition is misaligned.

According to the above embodiment, one detection sensor is composed of the one detection pixel 65 of the same size as the pixel 45. Thus, in contrast to the U.S. Pat. No. 6,952,465 having the striped dose detection sensors of 500 pixels, no density step that is visible to a human eye occurs in the X-ray image, and there is little fear of degradation in the image quality of the X-ray image. Also, the small-sized detection pixels 65 facilitate the defect correction.

Note that, the detection pixel 65 is treated as the defect pixel, and interpolated with the pixel values of the pixels 45 in the vicinity thereof. In this interpolation (defect correction), correction accuracy is increased with reduction in size of the detection pixel 65, so the smaller the size of the detection pixel 65 the better in terms of the image quality. On the other hand, the smaller the size of the detection pixel 65, the severer the effect of the positions of the X-ray absorbing portions 33 of the grid 18 becomes. In other words, focusing attention on the one detection pixel 65, there is a demerit that the misalignment in the geometrical disposition with the grid 18 increases the variation range of the output value. However, according to the present invention, by making the arrangement period S1 differ from the arrangement period F, the output values of the plurality of detection pixels 65 can be distributed even if the output value of each individual detection pixel 65 has the large variation range. Furthermore, not all the detection pixels 65 have a maximum output value Dmax or a minimum output value Dmin. In the AEC, the output values of the plurality of detection pixels 65 are averaged. Therefore, if reduction in size of each detection pixel 65 increases the variation range of each individual output value, the stable AEC can be carried out.

Moreover, since the detection pixels 65 are arrayed at the constant period, an algorithm for defect correction processing is easily simplified as compared with the case of an aperiodic arrangement. Also, the detection pixels 65 are easily formed in manufacturing. This brings about the merit of reduced manufacturing costs.

Also, the arrangement periods S1 and S2 of the detection pixels 65 in the X2 and Y2 directions are equalized, and both the relation between the arrangement period S1 and the arrangement period F and between the arrangement period S2 and the arrangement period F satisfies "arrangement period S1, S2≠N·arrangement period F" (N is an integer). Thus, the stable AEC can be carried out in either of cases where the grid 18 is used in such a position that the arrangement direction X1 of the grid 18 coincides with the X2 direction of the imaging surface 36 and where the grid 18 is used in such a position that the arrangement direction X1 of the grid 18 coincides with the Y2 direction of the imaging surface 36.

In a case where the electronic cassette 16 is in the shape of a square in plane, just as with this embodiment, it is difficult to recognize at sight whether the electronic cassette 16 is in a vertical position in which the X2 direction is in parallel with a horizontal direction or a horizontal position in which the Y2 direction is in parallel with the horizontal direction. Applying the striped dose detection sensors described in the U.S. Pat. No. 6,952,465 to such a square electronic cassette 16 and grid 18 impairs usability, because it is necessary to carefully confirm that the stripe direction of the dose detection sensors is not in parallel with the stripe direction of the grid 18. Especially, since the position cannot be confirmed in a state of setting the electronic cassette 16 in the holder 30*a*, the electronic cassette 16 has to be taken out of the holder 30*a* and this further impairs the usability. However, according to this embodiment, making neither of the arrangement periods S1 and S2 of the detection pixels 65 in the X2 and Y2 directions coincide with the arrangement period F improves convenience, because of eliminating the need for carefully confirming the position of the electronic cassette 16 and the position of the grid 18.

Note that, the arrangement periods S1 and S2 of the detection pixels 65 are not necessarily the same. This is because as long as each of the arrangement periods S1 and S2 is different from the arrangement period F, the average of the detection pixels 65 has the small variation range and the stable AEC can be carried out.

However, it is preferable that the arrangement period S2 and the arrangement period S1 be the same. This is because whether or not the stable AEC can be carried out depends on the relation between the arrangement period S1, S2 and the arrangement period F. Thus, depending on the type (grid density) of the grid 18, the arrangement period S1, S2 may possibly coincide with the arrangement period F and the stable AEC may not be carried out with the grid 18. Therefore, in performing grid imaging with the electronic cassette 16, it is necessary to investigate on a grid-type by grid-type basis whether or not the stable AEC can be carried out by combination with the electronic cassette 16. Such an investigation operation is performed based on the arrangement periods S1 and S2 and the grid density of the grid 18. Equalizing the arrangement periods S1 and S2 eliminates the need for performing the investigation as to each of the arrangement periods S1 and S2, and hence improves convenience. Also, if the arrangement periods S1 and S2 are different from each other, whether or not the stable AEC can be carried out may depend on the position of the electronic cassette 16 even with the use of the same grid 18. Therefore, the usability deteriorates as compared with the case of equalizing the arrangement periods S1 and S2.

Also, if the arrangement periods S1 and S2 are different from each other, for example, it is conceivable that the number of the detection pixels 65 included in each of the measurement areas Aa and Ab of the same size may vary depending on the vertical and horizontal position of the electronic cassette 16. In this case, it becomes necessary to change an algorithm for calculating the integral value by using the detection pixels 65 in accordance with the orientation of the electronic cassette 16. Equalizing the arrangement periods S1 and S2 can share the algorithm, because the number of the detection pixels 65 included in the measurement area is invariable if the size of the measurement area is the same. For these reasons, the arrangement periods S1 and S2 are preferably equal to each other.

The electronic cassette 16 and the grid 18 in the shape of a square in plane are described in the above embodiment, but the electronic cassette and the grid may be in the shape of a rectangle in plane. As the electronic cassette in the shape of a rectangle in plane, for example, there is an electronic cassette of a size compatible with the International Standard ISO 4090:2001, just as with a film cassette and an IP (imaging plate) cassette.

Also in the case of the electronic cassette in the shape of a rectangle in plane, it is preferable that the arrangement periods S1 and S2 be equalized. The rectangular electronic cassette is sometimes used in such a manner that in imaging a chest of a patient of typical physique, the electronic cassette is disposed such that a longitudinal direction of the electronic cassette is along a height direction of the patient, while in imaging a chest of a patient of corpulent physique, the electronic cassette is disposed in a state of being turned 90° such that the longitudinal direction is along a width direction of the patient's body. If the striped dose detection sensors according to the U.S. Pat. No. 6,952,465 are used in this rectangular electronic cassette, the 90° turn of the electronic cassette brings about the coincidence between the stripe direction of the dose detection sensors and the stripe direction of the grid, even though the stripe direction of the dose detection sensors is orthogonal to the stripe direction of the grid in imaging of the patient of the typical physique. However, making the arrangement period S1, S2 of the detection pixels 65 in the X2 or Y2 direction differ from the arrangement period F, as described in this embodiment, prevents the occurrence of this problem.

Second Embodiment

Figure 18:
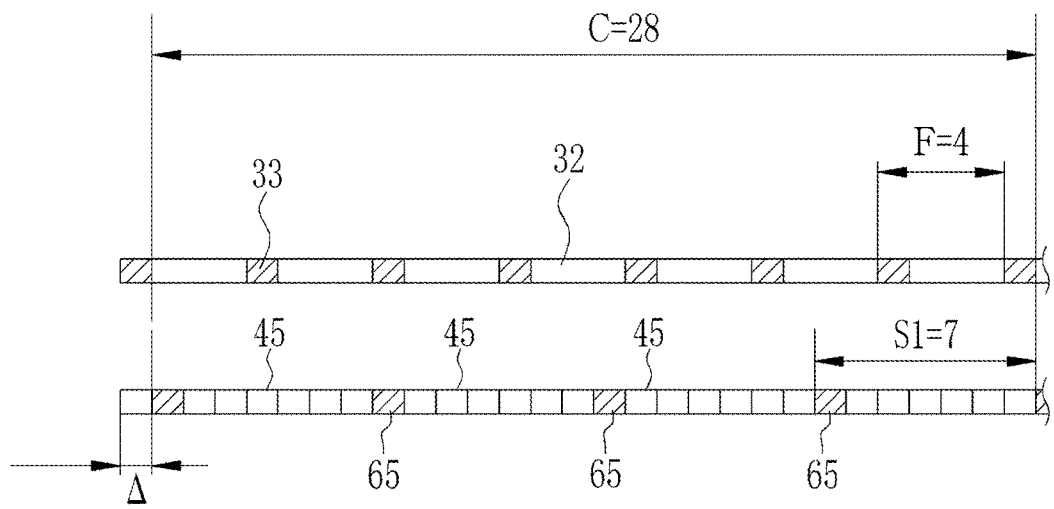
FIG. 18 is an explanatory view of a first example of a second embodiment.
Figure 19:
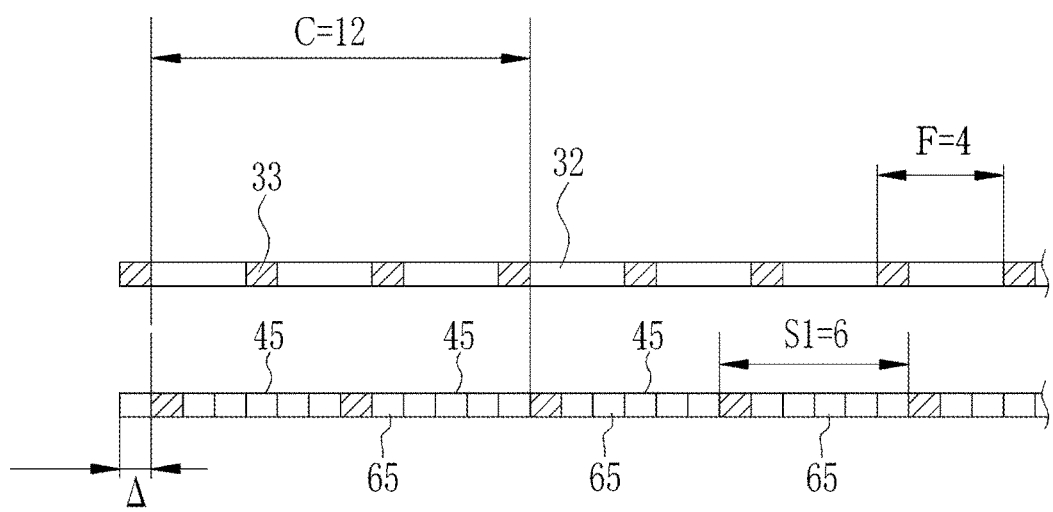
FIG. 19 is an explanatory view of a second example of the second embodiment.

In a second embodiment shown in FIGS. 18 and 19, each of the arrangement period S1 and the arrangement period F is represented as a length in unit of the number of the pixels 45. In FIG. 18, the arrangement period S1 is 7 because there is space of six pixels 45 between the two detection pixels 65. The arrangement period F has a length of four pixels 45, so a conversion value, being the number of pixels 45 into which the arrangement period F is converted, is 4. In an example shown in FIG. 19, the arrangement period S1 is 6, and the arrangement period F is 4.

Both of FIGS. 18 and 19 satisfy the relation of arrangement period S1≠the arrangement period F, and hence represent embodiments included in the present invention. However, comparing between FIGS. 18 and 19, an example of FIG. 18 is more preferable. The reason is as follows. In the example of FIG. 18, since the arrangement period S1 of the detection pixels 65 is 7 and the arrangement period F is 4, the arrangement period S1 and the arrangement period F are co-prime numbers. On the contrary, in the example of FIG. 19, since the arrangement period S1 of the detection pixels 65 is 6 and the arrangement period F is 4, the arrangement period S1 and the arrangement period F are not co-prime numbers.

As shown in FIG. 8, how the X-ray absorbing portions 33 overlap with the plurality of detection pixels 65 varies in accordance with the position of each detection pixel 65, such that one detection pixel 65 has a large overlap amount with the X-ray absorbing portion 33, while anther detection pixel 65 has a small overlap amount. However, since both of the X-ray absorbing portions 33 and the detection pixels 65 are arrayed periodically, an overlap state is in cycles with an overlap period C. The overlap period C is a least common multiple of the arrangement period S1 and the arrangement period F. The number of the detection pixels 65 included in the overlap period C is increased with the length of the overlap period C. The larger the number of the detection pixels 65 included in the overlap period C, the more the output value of each detection pixel 65 is distributed. Therefore, the output value of each detection pixel 65 is leveled, and the stable AEC can be carried out.

In the case of the example of FIG. 19, the overlap period C is the least common multiple (12) of the arrangement period S1 (6) and the arrangement period (4). In the example of FIG. 19, since the arrangement period S1 (6) and the arrangement period F (4) are not co-prime numbers, the overlap period C is less than the product (4×6=24) of the arrangement period S1 (6) and the arrangement period (4). In the case of the example of FIG. 19, the number of the detection pixels 65 included in the overlap period C is 2, given by dividing the least common multiple (12) by a pixel period (6) of the arrangement period S1.

On the other hand, in the case of the example of FIG. 18, since the arrangement period S1 (7) and the arrangement period F (4) are co-prime numbers, the least common multiple is 7×4=28, and hence the overlap period C is 28. Thus, the overlap period C is equal to the product (7×4=28) of the arrangement period S1 (7) and the arrangement period F (4). In the example of FIG. 18, the number of the detection pixels 65 included in the overlap period C is 4, given by dividing the least common multiple (28) by a pixel period (7) of the arrangement period S1.

Comparing the examples of FIGS. 18 and 19, since the overlap period C (28) of the co-prime numbers shown in FIG. 18 is longer than the overlap period (12) of the not co-prime numbers shown in FIG. 19, the number (4) of the detection pixels 65 included in the overlap period C of the example of FIG. 18 is larger than the number (2) of the detection pixels 65 included in the overlap period C of the example of FIG. 2. The overlap period C is repeated, so the larger the number of the detection pixels 65 included in the overlap period C, the more the output value of the detection pixel 65 is distributed. Thus, the variation range of the average of the output values of the detection pixels 65 is easily reduced. Accordingly, it is preferable that the arrangement period S1 and the arrangement period F are co-prime numbers, just as in the case of FIG. 18.

Other embodiments of the detection panel 35a will be hereinafter described. In each embodiment, the same reference numerals as those of the first and second embodiments indicate the same components as those of the first and second embodiments, and detailed description thereof will be omitted.

Third Embodiment

Figure 20A:
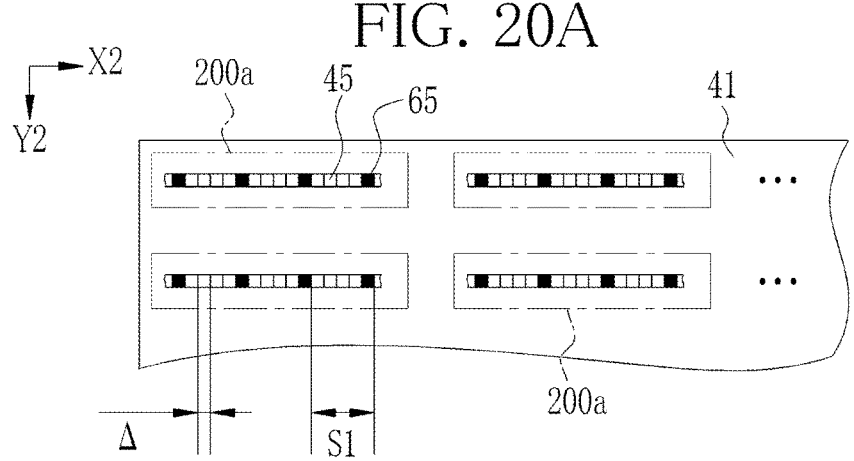
FIG. 20A is an explanatory view of a first mode of a first example of a third embodiment.
Figure 20B:
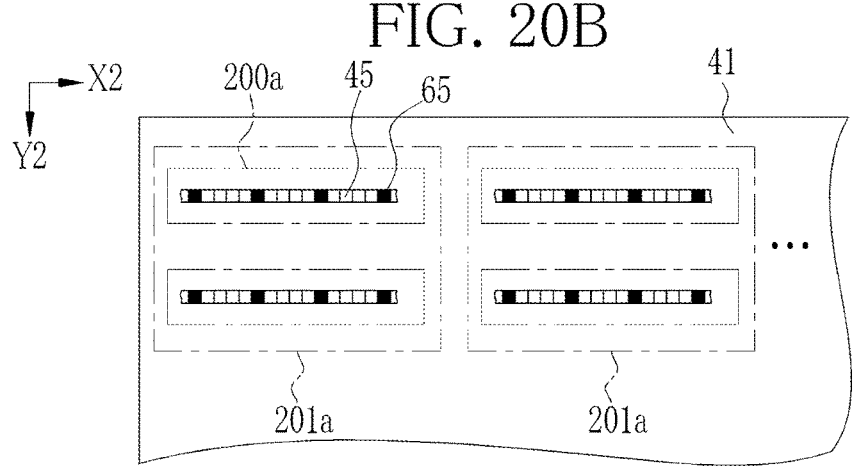
FIG. 20B is an explanatory view of a second mode of the first example of the third embodiment.
Figure 20C:
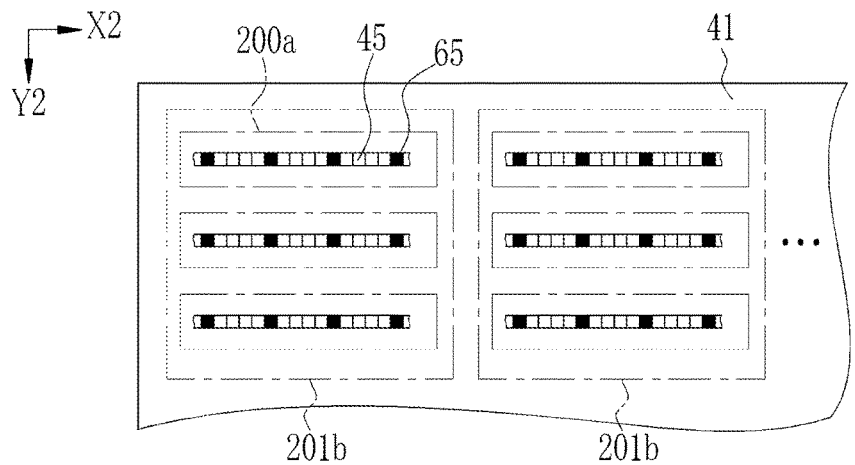
FIG. 20C is an explanatory view of a third mode of the first example of the third embodiment.
Figure 21:
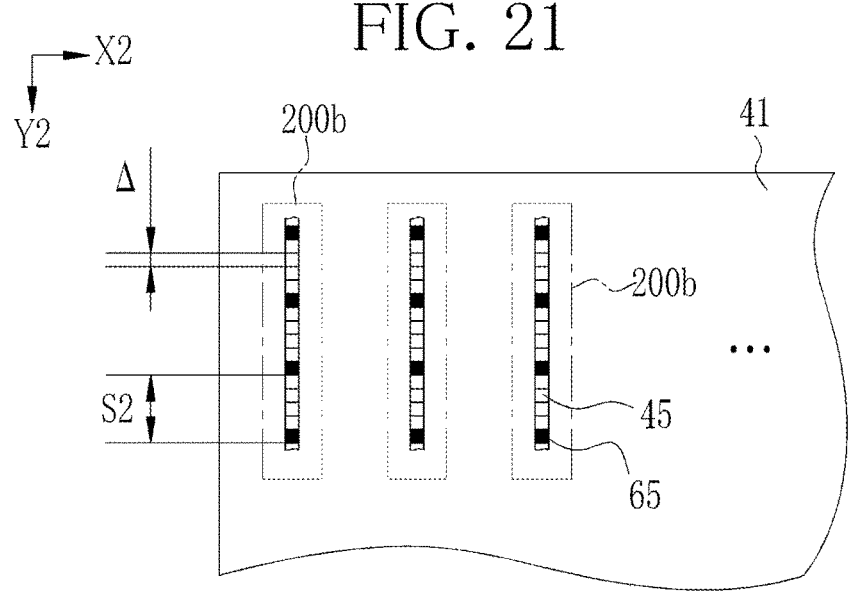
FIG. 21 is an explanatory view of a second example of the third embodiment.
Figure 22:
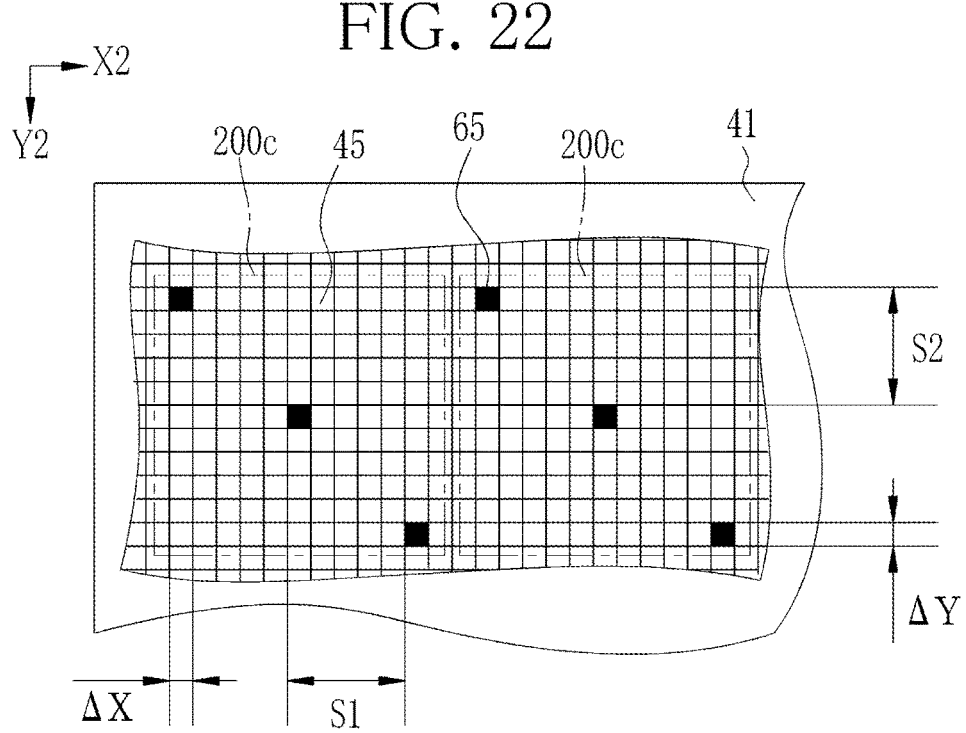
FIG. 22 is an explanatory view of a third example of the third embodiment.

In a third embodiment shown in FIGS. 20 to 22, an array of the detection pixels 65 in which the average of the dose detection signals of the detection pixels 65 is calculated is grouped into one set 200. The sets 200 are periodically arranged in the same or different rows, so as to arrange the sets 200 over the entire imaging surface 36 in a distributed manner. The set 200 is a minimum unit of a group of the detection pixels 65 in which the AEC section 67 calculates the average of the dose detection signals. Note that, the sets 200 may be arranged intensively in a region corresponding to the measurement area set in advance, such as left and right lung fields, for example, instead of being arranged over the entire imaging surface 36.

A set 200a shown in FIG. 20A is an example in which a plurality of detection pixels 65 (four detection pixels 65 in this example) is arrayed in one row extending in the X2 direction at an arrangement period S1=5, and the sets 200a are regularly arranged at equal intervals, for example. The set 200a is a minimum unit of a group of the detection pixels 65 in which the AEC section 67 calculates the average of the dose detection signals. Accordingly, a block 201a that is formed with the two sets 200a and has the eight detection pixels 65 as shown in FIG. 20B, or a block 201b that is formed with three sets 200a and has the twelve detection pixels 65 as shown in FIG. 20C may be established as a minimum unit for calculating the average. The intervals between the sets 200a or between the blocks 201a or 201b may be irregular.

Also, as shown in FIG. 21, a set 200b in which the detection pixels 65 are arrayed in the Y2 direction may be used. In the set 200b, each of the pixel pitch Δ and the arrangement period S2 of the detection pixels 65 is a length in the Y2 direction. Also, the sets 200a each having the detection pixels 65 arrayed in the X2 direction as shown in FIG. 20A and the sets 200b each having the detection pixels 65 arrayed in the Y2 direction may be mixed in the imaging surface 36. Selectively using either the sets 200a or the sets 200b in accordance with the attachment position of the grid 18 makes it possible to carry out the stable AEC, irrespective of the attachment position.

The set 200a shown in FIG. 20A or the set 200b shown in FIG. 21 is a set that is composed of a plurality of detection pixels 65 arrayed in one row or one column. However, as a set 200c shown in FIG. 22, a set may be composed of a plurality of the detection pixels 65 arranged with being shifted in the X2 and Y2 directions.

In the set 200c shown in FIG. 22, the plurality of detection pixels 65 is arrange in the different rows, and as for the X2 direction at an arrangement period S1=5 with leaving space of four columns. Although the detection pixels 65 are situated in the different rows, the output value of each detection pixel 65 is distributed as long as the arrangement period 51 in the X2 direction is different from the arrangement period F, so the average has a reduced variation range. As described above, even in a case where the detection pixels 65 are situated in the different rows, the arrangement period S1 of the detection pixels 65 can be obtained just as in the case of arranging a plurality of detection pixels 65 in one row, and the arrangement period S1 corresponds to a length in the X2 direction (row direction).

As for the X2 direction, the pixel pitch ΔX and the arrangement period S1 of the detection pixels 65 in the set 200c coincide with the pixel pitch Δ and the arrangement period S1 of the detection pixels 65 in the set 200a shown in FIG. 20A. Thus, the average of the output values of a group of the detection pixels 65 in the set 200c is approximately equal to the average of the output values of the group of the detection pixels 65 in the set 200a, and therefore the set 200c may be substituted for the set 200a.

Also, as for the Y2 direction, the plurality of detection pixels 65 in the set 200c is arranged at an arrangement period S2=5, though being situated in the different columns. Although the detection pixels 65 are situated in the different columns, the output value of each detection pixel 65 is distributed as long as the arrangement period S2 in the Y2 direction is different from the arrangement period F, so the average has a reduced variation range. As for the Y2 direction, the pixel pitch ΔY and the arrangement period S2 of the detection pixels 65 in the set 200c coincide with the pixel pitch Δ and the arrangement period S2 of the detection pixels 65 in the set 200b shown in FIG. 21. Thus, the set 200c may be substituted for the set 200b. As described above, even in a case where the detection pixels 65 are situated in the different columns, the arrangement period S2 of the detection pixels 65 can be obtained just as in the case of arranging a plurality of the detection pixels 65 in one column, and the arrangement period S2 corresponds to a length in the Y2 direction (column direction).

The set 200c is usable instead of both the set 200a shown in FIG. 20A and the set 200b shown in FIG. 21. Thus, providing the sets 200c allows carrying out the stable AEC irrespective of the attachment position of the grid 18, just as in the case of providing the sets 200a and the sets 200b in a mixed manner. Furthermore, in the case of mixing the sets 200a and 200b, it is necessary to selectively use the sets

200a or 200b in accordance with the attachment position of the grid 18. However, using the sets 200c eliminates the need for the selective use in accordance with the attachment position of the grid 18. Also, the use of the sets 200c can reduce the number of the detection pixels 65 in half, as compared with the case of mixing the sets 200a and 200b.

As the detection pixel 65 of this example, a short circuit between the photodiode 46 and the signal line 52 causes a continuous flow of the electric charge of the detection pixel 65 through the signal line 52. Thus, even if the detection pixels 65 are situated in the different rows, the electric charge of the detection pixels 65 flows into the integrating amplifiers 60 of the signal processing circuit 54 at approximately the same time. Therefore, there is a merit that the dose detection signals of the detection pixels 65 in the set 200c can be read out at the same time.

Note that, in the set 200c of this example, a shift amount (five pixels) of the detection pixels 65 is the same in the X2 and Y2 directions, but may be different between the X2 direction and the Y2 direction.

Fourth Embodiment

Figure 23:
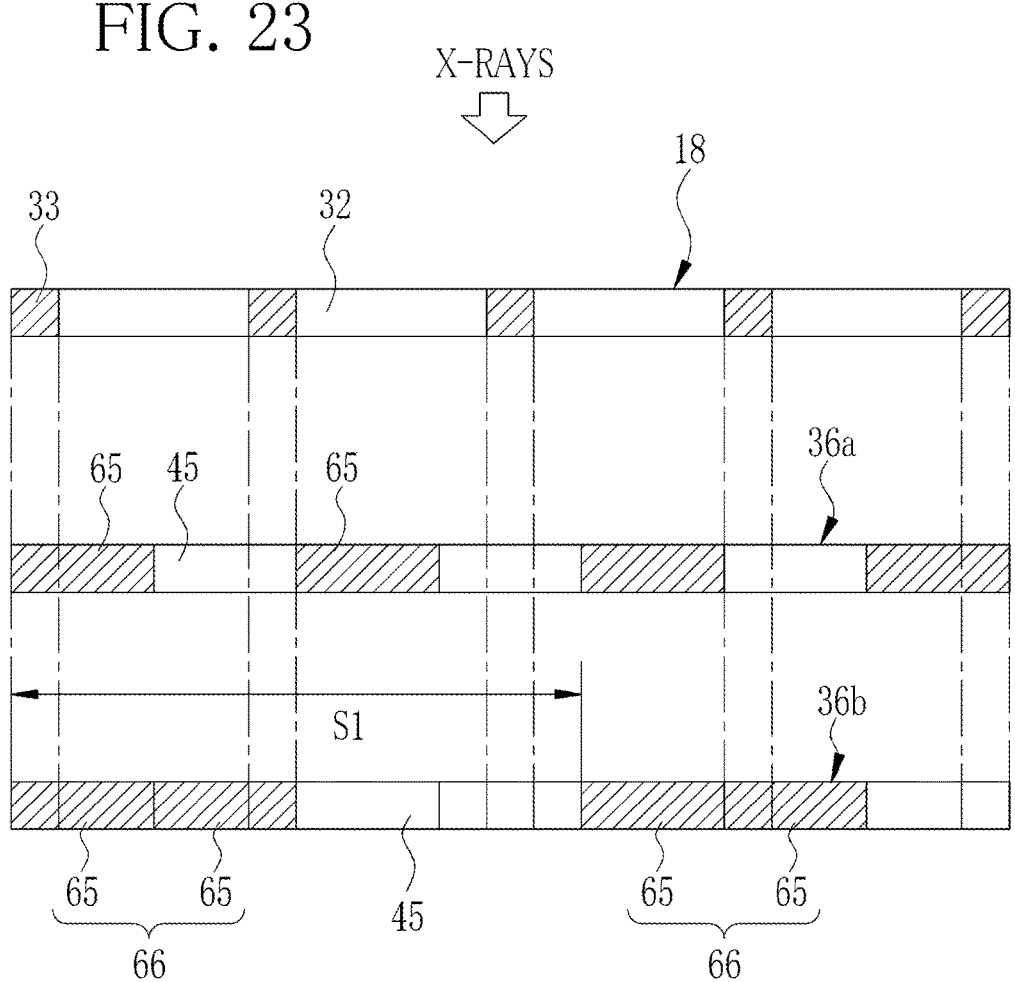
FIG. 23 is an explanatory view of detection pixel groups according to a fourth embodiment.

In each of the above embodiments, one detection pixel composes one dose detection sensor. However, one dose detection sensor may be composed of a detection pixel group 66 including a plurality of adjoining detection pixels 65, as shown in FIG. 23. In a case where the dose detection sensor is composed of the detection pixel group 66, the arrangement period S1 corresponds to an arrangement period of the plurality of detection pixel groups 66 that is periodically arranged with leaving space.

FIG. 23 shows a state of viewing the grid 18 and the imaging surface 36 of the detection panel 35a from a side (Y1 and Y2 directions), just as with FIG. 8 and the like. The individual detection pixel 65 is used as the dose detection sensor in an imaging surface 36a, while the detection pixel group 66 including the two adjoining detection pixels 65 is used as the dose detection sensor in an imaging surface 36b. The detection pixels 65 and the X-ray absorbing portions 33 are hatched for the purpose of distinction.

For example, the width of the X-ray transmitting portion 32 of the grid 18 in the X1 direction is 200 μm, and the width of the X-ray absorbing portion 33 thereof is 50 μm. The width of the detection pixel 65 in the same direction is 150 μm. The ratio of the X-ray transmitting portion 32 to an area of the detection pixel 65 in the imaging surface 36a is in a range of 2/3 to 1. The ratio of the X-ray transmitting portion 32 to an area of the detection pixel group 66 in the imaging surface 36b is in a range of 4/6 to 5/6. According to the area ratios, provided that the X-rays of the same dose is detected, the maximum output difference between the maximum output value and the minimum output value of the detection pixel 65 in the imaging surface 36a is 1÷2/3=1.5, while the maximum output difference of the detection pixel group 66 in the imaging surface 36b is 5/6÷4/6=1.25.

As described above, using the detection pixel group 66 as the dose detection sensor reduces the maximum output difference of the dose detection signal, as compared with the case of using the one detection pixel 65 as the one dose detection sensor. The smaller the maximum output difference, the smaller the variation range of the output value becomes. Accordingly, if the geometrical disposition between the grid 18 and the detection panel 35a is misaligned, the variation range of the output value of each individual detection pixel group 66 is smaller than that of the one detection pixel 65. Thus, the output value becomes stable, and the stable AEC can be carried out without being affected by the misalignment in the geometrical disposition. Also, the detection pixel group 66 has an increased signal amount of the dose detection signal because the detection pixel group 66 is larger than the detection pixel 65 in size, and an S/N ratio is improved. Note that, in a case where the one detection pixel group 66 composes the one dose detection sensor, the detection pixel group 66 preferably includes a number of pixels that are at an invisible level after the defect correction, and more preferably on the order of ten pixels. This size of dose detection sensor is much smaller than the striped dose detection sensors of five hundred pixels according to the U.S. Pat. No. 6,952,465, and does not cause degradation in the image quality of the X-ray image.

Note that, the detection pixel group 66 is composed of the plurality of detection pixels 65 adjoining in the X2 direction in an example of FIG. 23, but in a like manner, the detection pixel group 66 may be composed of a plurality of detection pixels 65 adjoining in the Y2 direction or both the X2 and Y2 directions. In a case where the one detection pixel group 66 composes the one dose detection sensor, as shown in FIG. 23, the arrangement period S1, S2 corresponds to a distance between the two detection pixel groups 66. In the case of FIG. 23, the arrangement period S1 is 4.

In each of the above embodiments, the pixels 45 for image detection and the detection pixels 65 functioning as the dose detection sensors are independent of each other and the detection pixels 65 are read out in a destructive manner, so portions of the detection pixels 65 become so-called point defects. However, since the size of one pixel is small enough, it is known as a result of experiment that performing interpolation processing by which pixel values of a column having the detection pixel 65 are interpolated with pixel values of adjoining columns without having the detection pixel 65 makes the defect hard to see by a human eye, and hence there is no substantial problem. However, it is best to prevent the occurrence of the point defects, and hence adopting a detection panel 100 having structure as shown in FIG. 24 can eliminate the need for performing the interpolation processing as the defect correction.

Fifth Embodiment

Figure 24:
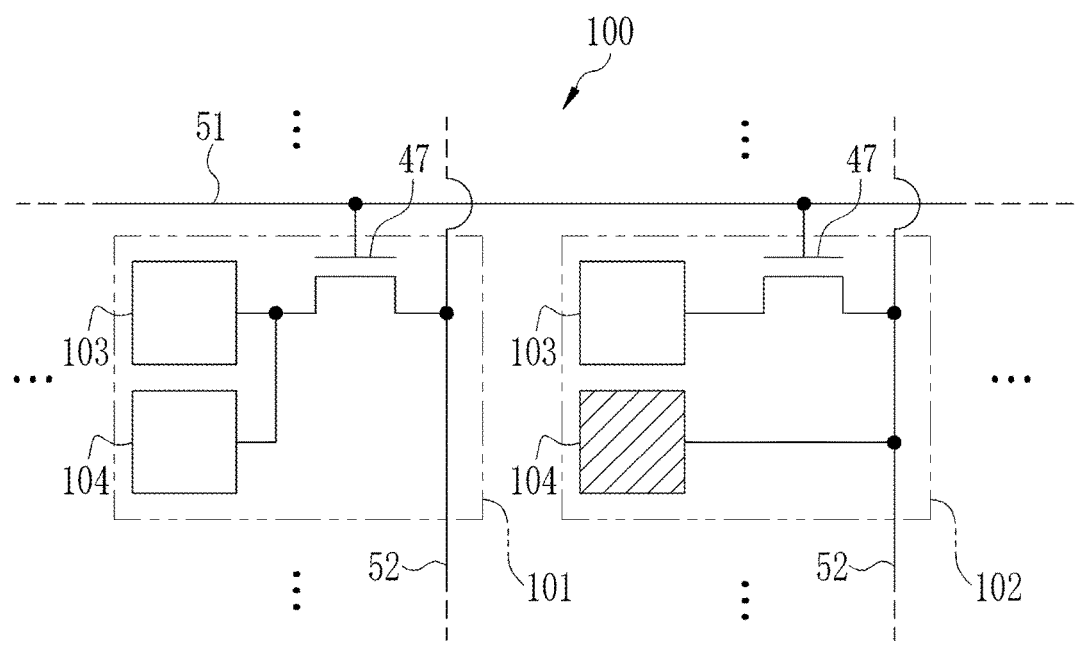
FIG. 24 is an explanatory view of a detection panel according to a fifth embodiment.

In FIG. 24, the detection panel 100 includes first pixels 101 for specific use in image detection and second pixels 102 for use in both the image detection and the AEC. The first and second pixels 101 and 102 are arranged into a matrix at an appropriate ratio, just as with the pixels 45 and the detection pixels 65 of the above embodiments. An arrangement period of the second pixels 102 is different from the arrangement period of the X-ray absorbing portions 33 of the grid 18. Each of the first and second pixels 101 and 102 has two photodiodes 103 and 104. The photodiodes 103 and 104 of the first pixel 101 are connected in parallel, and one end is connected to the signal line 52 through the TFT 47. In the second pixel 102, on the other hand, one end of the photodiode 103 is connected to the signal line 52 through the TFT 47, just as with that of the first pixel 101, but the photodiode 104 is directly connected to the signal line 52 without passing through the TFT 47. In other words, the photodiode 104 of the second pixel 102 has the same structure as the detection pixel 65 of the above embodiments.

From the first pixel 101, electric charge accumulated in the two photodiodes 103 and 104 is read out. From the second pixel 102, on the other hand, electric charge accumulated only in the photodiode 103 is read out. In the second pixel 102, electric charge produced in the photodiode 104 is used for the AEC and does not contribute production of the X-ray image. Thereby, provided that the photodiodes 103 and 104 have the same opening size, the amount of accumulated electric charge of the second pixel 102 is approximately half of that of the first pixel 101 under the same incident dose. However, it is possible to prevent degradation in the image quality of the X-ray image, as compared with the above embodiments in which no pixel value is obtained from the positions of the detection pixels 65 and the interpolation processing is absolutely necessary. A coefficient or the like that converts a pixel value of the second pixel 102 into a value corresponding to a pixel value of the first pixel 101 by multiplication is calculated in advance based on the opening size and the like of the photodiodes 103 and 104. Multiplying an output of the second pixel 102 by the coefficient can produce the X-ray image without performing the interpolation processing, and almost completely eliminate an adverse effect on the image equality of the X-ray image that is caused by using a part of the pixel for the AEC.

Sixth Embodiment

Figure 25:
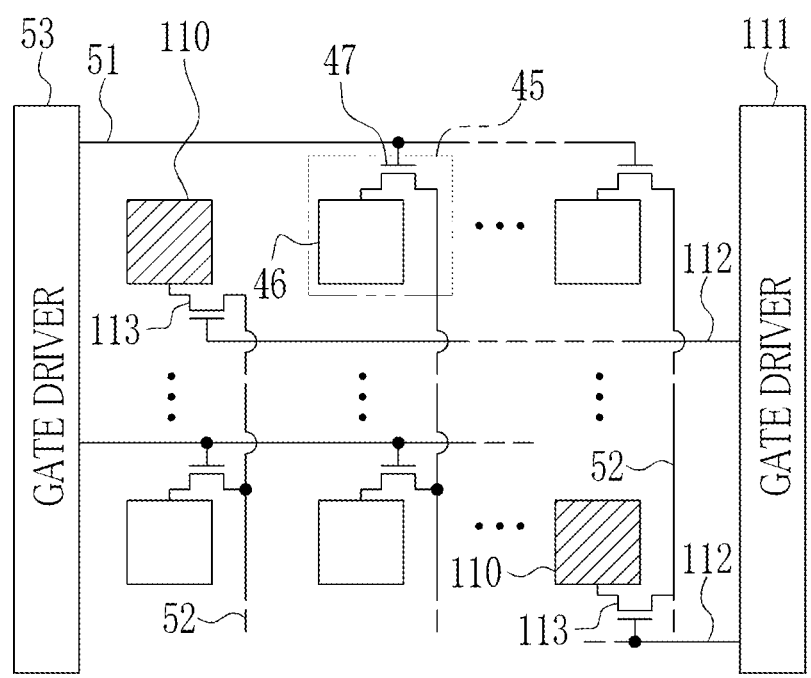
FIG. 25 is an explanatory view of a detection panel according to a sixth embodiment.

In the above first embodiment, the detection pixel 65 that is directly connected to the signal line 52 without passing through the TFT 47 is used as the dose detection sensor. However, as shown in FIG. 25, for example, a detection pixel 110 may be connected to a TFT 113 driven by a gate driver 111 and a scan line 112 that are different from the gate driver 53 and the scan lines 51 of the normal pixels 45. Electric charge accumulated in the detection pixel 110 can be read out independently of the normal pixels 45.

Seventh Embodiment

Alternatively, with taking advantage of the fact that an electric current that is based on electric charge produced in the pixel 45 flows through the bias line 48 for supplying the bias voltage Vb to each pixel 45, an electric current flowing through the bias line 48 connected to the specific pixel 45 may be monitored to detect the radiation dose. In another case, the radiation dose may be detected based on a leak current leaked from the pixel 45 in a state where all the TFTs 47 are turned off. Furthermore, a dose detection sensor for independent AEC having different structure may be provided in the same plane as the imaging surface 36, separately from the pixels 45. The same plane includes a case where the dose detection sensor is stacked on the TFT active matrix substrate having the TFTs 47 as another layer for the AEC, a case where the dose detection sensor is provided on a side opposite from the TFTs 47 relative to the scintillator, and the like. The dose detection sensor can be provided in any surface, as long as the surface is orthogonal to an X-ray incident direction and in parallel with the TFT active matrix substrate. However, in the case of the dose detection sensor for the independent AEC, the dose detection sensor is preferably in size of an invisible level. More specifically, the dose detection sensor is on the order of ten pixels in size.

In each of the above embodiments, in the AEC, the average of the output values of the plurality of dose detection sensors is calculated, and the integral value of the average is compared with the emission stop threshold value. However, a median or a sum is calculated instead of the average of the output values of the plurality of dose detection sensors, and an integral value of the median or the sum may be compared with the emission stop threshold value. According to the present invention, since the output values of the plurality of dose detection sensors are distributed, the use of the median or the sum can obtain the same effect as in the case of the average.

Each of the above embodiments is described with taking the electronic cassette, being the portable type X-ray image detecting device, as an example, but the present invention may be applied to a stationary type X-ray image detection device contained in the imaging stand. The console 17 and the electronic cassette 16 are separate from each other, but the console 17 is not necessarily an independent device, and the electronic cassette 16 may has the function of the console 17. In a like manner, the source control device 14 and the console 17 may be integrated in one unit.

In each of the above embodiments, the positions of the detection pixels 65 are already known in manufacturing the image detector 35, and the image detector 35 stores the position (coordinates) of every detection pixel 65 in a non-volatile memory (not shown) in advance, but this is not essential. To be more specific, every pixel 45 may be read out in a non-destructive manner, and pixels to be used as the detection pixels may be chosen from all the pixels 45 at any time to read out output values therefrom. For example, in response to choice of the body part to be imaged in an imaging menu, the pixels 45 in needed position are appropriately chosen as the detection pixels. At this time, the detection pixels may be chosen from the pixels 45 such that the arrangement period S1, S2 of the detection pixels or the detection pixel groups does not coincide with the arrangement period F.

The present invention is not limited to each of the above-described embodiments, and, as a matter of course, is modified into various configurations within the scope of the present invention. The present invention is applicable to an imaging system using another type of radiation such as γ-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device for carrying out imaging by using a scattered radiation removing grid having radiation absorbing portions for absorbing radiation and radiation transmitting portions for transmitting said radiation alternately and periodically arranged in a first direction, said radiation image detecting device comprising:
    a detection panel having an imaging surface provided with a plurality of pixels for converting said radiation into an electric signal, for detecting a radiographic image of an object;
    a plurality of dose detection sensors provided for performing exposure control of said radiographic image, said plurality of dose detection sensors being disposed in said imaging surface periodically with leaving space in said first direction, for detecting a dose of said radiation passed through said object and outputting a signal in accordance with said dose; and
    an arrangement period of said radiation absorbing portions being different from an arrangement period of said plurality of dose detection sensors in said first direction in said imaging surface,
    wherein an arrangement period of said dose detection sensors in a second direction orthogonal to said first direction is also different from said arrangement period of said radiation absorbing portions.

2. The radiation image detecting device according to claim 1, wherein said arrangement period of said dose detection sensors is not an integral multiple of said arrangement period of said radiation absorbing portions.

3. The radiation image detecting device according to claim 1, wherein each of said arrangement period of said dose detection sensors and said arrangement period of said radiation absorbing portions has a length in unit of the number of said pixels, and said arrangement periods are co-prime numbers.

4. The radiation image detecting device according to claim 1, wherein said arrangement period of said dose detection sensors in said second direction is the same as said arrangement period of said dose detection sensors in said first direction.

5. The radiation image detecting device according to claim 1, wherein a minimum size of said dose detection sensor is the same as the size of said pixel in said imaging surface.

6. The radiation image detecting device according to claim 1, wherein said dose detection sensors are detection pixels of which some of said pixels are utilized.

7. The radiation image detecting device according to claim 1, wherein
said radiation detection sensors are detection pixels as which some of said pixels are utilized; and
in a case where a plurality of said detection pixels are disposed with being shifted by one or more rows and one or more columns in each of a row direction corresponding to said first direction and a column direction corresponding to said second direction, an arrangement period in said first direction is a length in said row direction, and an arrangement period in said second direction is a length in said column direction.

8. The radiation image detecting device according to claim 6, wherein said dose detection sensor is a detection pixel group composed of a plurality of said detection pixels adjoining each other.

9. The radiation image detecting device according to claim 8, wherein said arrangement period of said dose detection sensors corresponds to an arrangement period of a plurality of said detection pixel groups arranged periodically with leaving space.

10. The radiation image detecting device according to claim 1, wherein
said dose detection sensor outputs said signal in accordance with said dose per unit of time; and
said radiation image detecting device further includes an automatic exposure control section for integrating an output value of said dose detection sensor, and comparing an integral value with an emission stop threshold value set in advance, and stopping emission of said radiation from a radiation source upon said integral value reaching said emission stop threshold value.

11. The radiation image detecting device according to claim 10, wherein said automatic exposure control section calculates an average of said output values of a plurality of said dose detection sensors, and obtains said integral value by integrating said calculated average.

12. The radiation image detecting device according to claim 1, wherein said scatter radiation removing grid is detachably attached.

13. A radiation imaging system for carrying out imaging by using a scattered radiation removing grid having radiation absorbing portions for absorbing radiation and radiation transmitting portions for transmitting said radiation alternately and periodically arranged in a first direction, said radiation imaging system comprising:
(A) a radiation generating device including a radiation source for emitting radiation; and
(B) a radiation image detecting device for detecting a radiographic image, including:
a detection panel having an imaging surface provided with a plurality of pixels for converting said radiation emitted from said radiation source into an electric signal, for detecting said radiographic image of an object;
a plurality of dose detection sensors provided for performing exposure control of said radiographic image, said plurality of dose detection sensors being disposed in said imaging surface periodically with leaving space in said first direction, for detecting a dose of said radiation passed through said object and outputting a signal in accordance with said dose; and
an arrangement period of said radiation absorbing portions being different from an arrangement period of said plurality of dose detection sensors in said first direction in said imaging surface,
wherein an arrangement period of said dose detection sensors in a second direction orthogonal to said first direction is also different from said arrangement period of said radiation absorbing portions.

* * * * *